US011666273B2

(12) United States Patent
Wilson et al.

(10) Patent No.: US 11,666,273 B2
(45) Date of Patent: Jun. 6, 2023

(54) ELECTRONIC DEVICE ENCLOSURE INCLUDING A GLASS CERAMIC REGION

(71) Applicant: Apple Inc., Cupertino, CA (US)

(72) Inventors: James R. Wilson, Cupertino, CA (US); Christopher D. Jones, Los Altos, CA (US); Tyler A. Marshall, Sunnyvale, CA (US)

(73) Assignee: APPLE INC., Cupertino, CA (US)

( * ) Notice: Subject to any disclaimer, the term of this patent is extended or adjusted under 35 U.S.C. 154(b) by 361 days.

(21) Appl. No.: 16/879,403

(22) Filed: May 20, 2020

(65) Prior Publication Data

US 2021/0361233 A1     Nov. 25, 2021

(51) Int. Cl.
*A61B 5/00*     (2006.01)
*H05K 5/00*     (2006.01)
(Continued)

(52) U.S. Cl.
CPC .......... *A61B 5/6802* (2013.01); *A61B 5/0075* (2013.01); *A61B 5/0077* (2013.01); *A61B 5/02433* (2013.01); *A61B 5/14552* (2013.01); *A61B 5/681* (2013.01); *A61B 5/6898* (2013.01); *A61B 5/742* (2013.01); *A61B 5/7475* (2013.01); *G01J 1/0204* (2013.01); *G01J 1/0214* (2013.01); *G01J 1/0407* (2013.01); *G01J 1/0474* (2013.01); *G01J 1/0488* (2013.01); *G01J 1/42* (2013.01);
(Continued)

(58) Field of Classification Search
CPC ... A61B 5/6802; A61B 5/0075; A61B 5/0077; A61B 5/742; A61B 5/7475; A61B 5/02433; A61B 5/14542; A61B 2562/0238; G01J 1/0407; G01J 1/42; G01J 3/42; G01J 3/108; G01J 5/05; H05K 5/0017; H05K 5/03; G06F 1/1616; G06F 1/163; G06F 3/041; H04N 5/2257
See application file for complete search history.

(56) References Cited

U.S. PATENT DOCUMENTS 2,795,084 A     6/1957   Littleton
3,410,673 A    11/1968   Marusak
(Continued)

FOREIGN PATENT DOCUMENTS

CN     101475300     7/2009
CN     103986803     8/2013
(Continued)

OTHER PUBLICATIONS

Aben et al., "A New Method for Tempering Stress Measurement in Glass Panels," Estonian Journal of Engineering, vol. 19, No. 4, pp. 292-297, 2013.
(Continued)

*Primary Examiner* — Jennifer D Bennett
*Assistant Examiner* — Erin R Garber
(74) *Attorney, Agent, or Firm* — Brownstein Hyatt Farber Schreck, LLP

(57) ABSTRACT

An electronic device including an optical component and an enclosure comprising a glass ceramic region is disclosed. The optical properties of the glass ceramic region and the positioning of the glass ceramic region with respect to the optical component can affect the performance of the optical component, the visual appearance of the optical component, or both.

20 Claims, 15 Drawing Sheets

(51) Int. Cl.

| | | |
|---|---|---|
| *H05K 5/03* | (2006.01) | |
| *G01J 1/42* | (2006.01) | |
| *G01J 1/04* | (2006.01) | |
| *G06F 1/16* | (2006.01) | |
| *A61B 5/024* | (2006.01) | |
| *A61B 5/1455* | (2006.01) | |
| *G01J 1/02* | (2006.01) | |
| *G06F 3/041* | (2006.01) | |
| *H04N 23/57* | (2023.01) | |

(52) U.S. Cl.
CPC .............. *H05K 5/0017* (2013.01); *H05K 5/03* (2013.01); *A61B 2562/0238* (2013.01); *G06F 1/163* (2013.01); *G06F 1/1616* (2013.01); *G06F 3/041* (2013.01); *H04N 23/57* (2023.01)

(56) References Cited

U.S. PATENT DOCUMENTS

| | | | |
|---|---|---|---|
| 3,433,611 | A | 3/1969 | Kubican |
| 3,464,880 | A | 9/1969 | Rinehart |
| 3,737,294 | A | 6/1973 | Dumbaugh, Jr. et al. |
| 3,746,526 | A | 7/1973 | Giffon |
| 3,899,315 | A | 8/1975 | Siegmund |
| 4,054,895 | A | 10/1977 | Ham et al. |
| 4,070,211 | A | 1/1978 | Haran et al. |
| 4,209,229 | A | 6/1980 | Rittler |
| 4,339,300 | A | 7/1982 | Noble et al. |
| 4,735,917 | A | 4/1988 | Flatley et al. |
| 4,849,299 | A | 7/1989 | Loth et al. |
| 5,122,177 | A | 6/1992 | Yoshizama et al. |
| 5,173,453 | A | 12/1992 | Beall et al. |
| 5,273,553 | A | 12/1993 | Hoshi et al. |
| 6,055,053 | A | 4/2000 | Lesniak |
| 6,067,005 | A | 5/2000 | DeVolpi |
| 6,169,256 | B1 | 1/2001 | Hanahara |
| 6,406,769 | B1 | 6/2002 | Delabre et al. |
| 6,809,278 | B2 | 10/2004 | Tsubaki |
| 6,928,224 | B2 | 8/2005 | Beall et al. |
| 7,115,827 | B2 | 10/2006 | Tseng |
| 7,240,519 | B2 | 7/2007 | Schwartz et al. |
| 7,459,199 | B2 | 12/2008 | Skeen |
| 7,497,093 | B2 | 3/2009 | Rosenflanz |
| 7,507,918 | B2 | 3/2009 | Kazama |
| 7,799,158 | B2 | 9/2010 | Yokoyama et al. |
| 7,902,474 | B2 | 3/2011 | Mittleman |
| 7,915,556 | B2 | 3/2011 | Ou |
| 7,966,785 | B2 | 6/2011 | Zadesky et al. |
| 8,003,217 | B2 | 8/2011 | Rosenflanz |
| 8,050,019 | B2 | 11/2011 | Wennemer |
| 8,092,737 | B2 | 1/2012 | Chang et al. |
| 8,212,455 | B2 | 7/2012 | Yura et al. |
| 8,277,704 | B2 | 10/2012 | Matsushima et al. |
| 8,379,159 | B2 | 2/2013 | Hsu |
| 8,431,849 | B2 | 4/2013 | Chen |
| 8,446,264 | B2 | 5/2013 | Tanase |
| 8,665,160 | B2 | 3/2014 | Uttermann et al. |
| 8,717,513 | B2 | 5/2014 | Park et al. |
| 8,783,065 | B2 | 7/2014 | Schillert et al. |
| 8,840,997 | B2 | 9/2014 | Koyama et al. |
| 8,898,824 | B2 | 12/2014 | Neidich et al. |
| 9,001,503 | B1 | 4/2015 | Hibino |
| 9,030,440 | B2 | 5/2015 | Pope |
| 9,069,198 | B2 | 6/2015 | Kim et al. |
| 9,110,230 | B2 | 8/2015 | Koch, III et al. |
| 9,125,298 | B2 | 9/2015 | Russell-Clarke |
| 9,134,547 | B2 | 9/2015 | McCabe et al. |
| 9,140,522 | B1 | 9/2015 | Miller et al. |
| 9,154,678 | B2 | 10/2015 | Kwong et al. |
| 9,193,625 | B2 | 11/2015 | Bookbinder et al. |
| 9,232,672 | B2 | 1/2016 | Kwong |
| 9,242,889 | B2 | 1/2016 | Yamakaji et al. |
| 9,249,045 | B2 | 2/2016 | Gabel et al. |
| 9,263,209 | B2 | 2/2016 | Chen |
| 9,302,937 | B2 | 4/2016 | Gulati et al. |
| 9,321,677 | B2 | 4/2016 | Chang et al. |
| 9,359,251 | B2 | 6/2016 | Bookbinder et al. |
| 9,375,900 | B2 | 6/2016 | Tsuchiya et al. |
| 9,390,930 | B2 | 7/2016 | Rogers et al. |
| 9,392,706 | B2 | 7/2016 | Yoo et al. |
| 9,429,997 | B2 | 8/2016 | Myers et al. |
| 9,474,174 | B2 | 10/2016 | Motohashi |
| 9,516,149 | B2 | 12/2016 | Wright et al. |
| 9,522,836 | B2 | 12/2016 | Gulati et al. |
| 9,524,413 | B2 | 12/2016 | Kim |
| 9,632,537 | B2 | 4/2017 | Memering et al. |
| 9,674,322 | B2 | 6/2017 | Motohashi et al. |
| 9,678,540 | B2 | 6/2017 | Memering et al. |
| 9,697,409 | B2 | 7/2017 | Myers |
| 9,718,727 | B2 | 8/2017 | Bookbinder et al. |
| 9,728,349 | B2 | 8/2017 | Huang |
| 9,840,435 | B2 | 12/2017 | Ohara et al. |
| 9,846,473 | B1 | 12/2017 | Kalscheur et al. |
| 9,870,880 | B2 | 1/2018 | Zercoe |
| 9,890,074 | B2 | 2/2018 | Liu |
| 9,897,574 | B2 | 2/2018 | Roussev et al. |
| 9,902,138 | B2 | 2/2018 | Edwards |
| 9,902,641 | B2 | 2/2018 | Hall et al. |
| 9,941,074 | B2 | 4/2018 | Tu |
| 9,946,302 | B2 | 4/2018 | Franklin et al. |
| 9,963,374 | B2 | 5/2018 | Jouanno et al. |
| 10,133,156 | B2 | 11/2018 | Pilliod et al. |
| 10,141,133 | B2 | 11/2018 | Bae |
| 10,146,982 | B2 | 12/2018 | Hsu |
| 10,189,228 | B2 | 1/2019 | Couillard et al. |
| 10,206,298 | B2 | 2/2019 | Memering et al. |
| 10,286,631 | B2 | 5/2019 | Alder et al. |
| 10,318,783 | B2 | 6/2019 | Kang |
| 10,324,496 | B2 | 6/2019 | Kwong et al. |
| 10,357,945 | B2 | 7/2019 | Beall et al. |
| 10,425,994 | B2 | 9/2019 | Weiss et al. |
| 10,494,860 | B1 | 12/2019 | Jones et al. |
| 10,513,455 | B2 | 12/2019 | Cook et al. |
| 10,611,666 | B2 | 4/2020 | Jones et al. |
| 10,694,010 | B2 | 6/2020 | Jones et al. |
| 10,702,211 | B2 | 7/2020 | Clavelle et al. |
| 10,800,141 | B2 | 10/2020 | Bartlow et al. |
| 10,827,635 | B1 | 11/2020 | Limarga et al. |
| 10,875,277 | B2 | 12/2020 | Aoki et al. |
| 10,899,660 | B2 | 1/2021 | Luzzato et al. |
| 10,917,505 | B2 | 2/2021 | Jones et al. |
| 10,919,270 | B2 | 2/2021 | Oh et al. |
| 11,192,823 | B2 | 12/2021 | Li et al. |
| 11,199,929 | B2 | 12/2021 | Poole et al. |
| 2003/0040346 | A1 | 2/2003 | Fukuda et al. |
| 2003/0062490 | A1 | 4/2003 | Fujieda |
| 2004/0003627 | A1 | 1/2004 | Hashima |
| 2004/0041504 | A1 | 3/2004 | Ozolins |
| 2004/0105026 | A1 | 6/2004 | Campbell et al. |
| 2005/0135724 | A1 | 6/2005 | Helvajian |
| 2005/0176506 | A1 | 8/2005 | Goto |
| 2008/0049980 | A1 | 2/2008 | Castaneda |
| 2009/0040737 | A1 | 2/2009 | Shimura |
| 2010/0013786 | A1 | 1/2010 | Nishikawa et al. |
| 2010/0108486 | A1 | 5/2010 | Yoshida |
| 2010/0127420 | A1 | 5/2010 | Dannoux |
| 2010/0148996 | A1 | 6/2010 | Wang |
| 2010/0263708 | A1 | 10/2010 | Reichart et al. |
| 2010/0279068 | A1 | 11/2010 | Cook et al. |
| 2010/0285310 | A1 | 11/2010 | Izutani et al. |
| 2010/0330814 | A1 | 12/2010 | Yokota |
| 2011/0038115 | A1 | 2/2011 | Halkosaari |
| 2011/0041987 | A1 | 2/2011 | Hori et al. |
| 2011/0177300 | A1 | 7/2011 | Hankey et al. |
| 2011/0253520 | A1 | 10/2011 | Lim |
| 2012/0052271 | A1 | 3/2012 | Gomez et al. |
| 2012/0176760 | A1 | 7/2012 | Cohen et al. |
| 2012/0206669 | A1 | 8/2012 | Kim |
| 2012/0236526 | A1 | 9/2012 | Weber |
| 2012/0250273 | A1 | 10/2012 | Kuo |
| 2012/0327325 | A1 | 12/2012 | Park et al. |
| 2013/0128434 | A1 | 5/2013 | Yamamoto et al. |
| 2013/0236699 | A1 | 9/2013 | Prest et al. |
| 2014/0093702 | A1 | 4/2014 | Kitajima |

(56) References Cited

U.S. PATENT DOCUMENTS

| | | |
|---|---|---|
| 2014/0116090 A1 | 5/2014 | Lee et al. |
| 2014/0151320 A1 | 6/2014 | Chang et al. |
| 2014/0272298 A1 | 9/2014 | Memering et al. |
| 2014/0285956 A1 | 9/2014 | Russell-Clarke et al. |
| 2014/0311882 A1 | 10/2014 | Terashita |
| 2015/0002993 A1 | 1/2015 | Lee |
| 2015/0030834 A1 | 1/2015 | Morey et al. |
| 2015/0030859 A1 | 1/2015 | Rogers et al. |
| 2015/0044445 A1 | 2/2015 | Garner et al. |
| 2015/0077830 A1 | 3/2015 | Lin et al. |
| 2015/0093581 A1 | 4/2015 | Murata et al. |
| 2015/0104618 A1 | 4/2015 | Hayashi et al. |
| 2015/0122406 A1 | 5/2015 | Fisher et al. |
| 2015/0163382 A1 | 6/2015 | Kwong et al. |
| 2015/0165548 A1 | 6/2015 | Marjanovic et al. |
| 2015/0202854 A1 | 7/2015 | Tsuchiya et al. |
| 2015/0212247 A1 | 7/2015 | Borrelli et al. |
| 2015/0232366 A1 | 8/2015 | Fredholm et al. |
| 2015/0241732 A1 | 8/2015 | Kim et al. |
| 2015/0245514 A1 | 8/2015 | Choung |
| 2015/0274572 A1 | 10/2015 | Wada et al. |
| 2015/0299036 A1 | 10/2015 | Ukrainczyk et al. |
| 2016/0028931 A1 | 1/2016 | Kwong et al. |
| 2016/0137550 A1 | 5/2016 | Murata et al. |
| 2016/0224142 A1 | 8/2016 | Yang et al. |
| 2016/0270247 A1 | 9/2016 | Jones et al. |
| 2016/0357294 A1 | 12/2016 | Czeki et al. |
| 2016/0377768 A1 | 12/2016 | Wilson et al. |
| 2017/0059749 A1 | 3/2017 | Wakatsuki et al. |
| 2017/0066223 A1 | 3/2017 | Notsu et al. |
| 2017/0282503 A1 | 10/2017 | Peng et al. |
| 2017/0300114 A1 | 10/2017 | Matsuyuki et al. |
| 2017/0305788 A1 | 10/2017 | Nikulin |
| 2017/0334770 A1 | 11/2017 | Luzzato et al. |
| 2017/0340518 A1 | 11/2017 | Logunov et al. |
| 2017/0364172 A1 | 12/2017 | Kim et al. |
| 2018/0009697 A1 | 1/2018 | He et al. |
| 2018/0024274 A1 | 1/2018 | Rogers et al. |
| 2018/0067212 A1* | 3/2018 | Wilson .................. H04M 1/02 |
| 2018/0086026 A1 | 3/2018 | Nguyen et al. |
| 2018/0086663 A1 | 3/2018 | Luzzato et al. |
| 2018/0088399 A1 | 3/2018 | Fukushi et al. |
| 2018/0125756 A1 | 5/2018 | Gerrish et al. |
| 2018/0126704 A1 | 5/2018 | Zhang et al. |
| 2018/0134606 A1 | 5/2018 | Wagner et al. |
| 2018/0154615 A1 | 6/2018 | Dohn et al. |
| 2018/0237325 A1 | 8/2018 | Li et al. |
| 2018/0282207 A1 | 10/2018 | Fujii et al. |
| 2018/0304588 A1 | 10/2018 | Harris et al. |
| 2018/0304825 A1 | 10/2018 | Mattelet et al. |
| 2018/0326704 A1 | 11/2018 | Harris et al. |
| 2018/0370843 A1 | 12/2018 | Gross et al. |
| 2019/0022979 A1 | 1/2019 | Luzzato et al. |
| 2019/0030861 A1 | 1/2019 | Bellman et al. |
| 2019/0033144 A1 | 1/2019 | Andrews et al. |
| 2019/0037690 A1 | 1/2019 | Wilson et al. |
| 2019/0134944 A1 | 5/2019 | Dawson-Elli |
| 2019/0160787 A1 | 5/2019 | Bartlow et al. |
| 2019/0161402 A1 | 5/2019 | Harris et al. |
| 2019/0169060 A1 | 6/2019 | Jones et al. |
| 2019/0177215 A1 | 6/2019 | Jin et al. |
| 2019/0219463 A1 | 7/2019 | Orihara et al. |
| 2019/0263708 A1 | 8/2019 | Bookbinder et al. |
| 2019/0293838 A1 | 9/2019 | Haba et al. |
| 2020/0014780 A1 | 1/2020 | Jones et al. |
| 2020/0039186 A1 | 2/2020 | Yuan et al. |
| 2020/0055281 A1 | 2/2020 | Yoon et al. |
| 2020/0095159 A1 | 3/2020 | Marshall et al. |
| 2020/0301527 A1 | 9/2020 | Poole et al. |
| 2020/0323440 A1* | 10/2020 | Vule .................. A61B 5/02125 |
| 2020/0339472 A1 | 10/2020 | Yoon et al. |
| 2020/0346525 A1 | 11/2020 | Mannheim Astete et al. |
| 2020/0369560 A1 | 11/2020 | Takeda et al. |
| 2020/0407266 A1 | 12/2020 | Suzuki et al. |
| 2021/0009469 A1 | 1/2021 | Marshall et al. |
| 2021/0014992 A1 | 1/2021 | Limarga et al. |
| 2021/0016547 A1 | 1/2021 | Bartlow et al. |
| 2021/0033757 A1 | 2/2021 | Wilson et al. |
| 2021/0072789 A1 | 3/2021 | Rogers et al. |
| 2021/0303031 A1 | 9/2021 | Poole et al. |
| 2021/0361233 A1 | 11/2021 | Wilson et al. |
| 2022/0009823 A1* | 1/2022 | Dejneka .............. C03C 10/0027 |
| 2022/0117094 A1 | 4/2022 | Prest et al. |
| 2022/0193825 A1 | 6/2022 | Van Dyke et al. |
| 2022/0194840 A1 | 6/2022 | Meschke et al. |
| 2022/0194841 A1 | 6/2022 | Meschke et al. |
| 2023/0014168 A1 | 1/2023 | Poole et al. |

FOREIGN PATENT DOCUMENTS

| | | |
|---|---|---|
| CN | 104837781 | 8/2015 |
| CN | 105765722 | 7/2016 |
| CN | 106007345 | 10/2016 |
| CN | 106341962 | 1/2017 |
| CN | 106485275 | 3/2017 |
| CN | 108017263 | 5/2018 |
| CN | 108285263 | 7/2018 |
| CN | 108545917 | 9/2018 |
| CN | 108600419 | 9/2018 |
| CN | 108632510 | 10/2018 |
| CN | 110857865 | 3/2020 |
| CN | 111655478 | 9/2020 |
| CN | 215010334 | 12/2021 |
| DE | 102016107630 | 10/2017 |
| JP | S6042176 | 9/1985 |
| JP | S6271215 | 5/1987 |
| JP | H03122036 | 5/1991 |
| TW | 201912602 | 4/2019 |
| WO | WO2010/077845 | 7/2010 |
| WO | WO2012/027660 | 3/2012 |
| WO | WO2012/074983 | 6/2012 |
| WO | WO2014/022356 | 2/2014 |
| WO | WO2014/022681 | 2/2014 |
| WO | WO2015/031420 | 3/2015 |
| WO | WO2015/095089 | 6/2015 |
| WO | WO2016/065118 | 4/2016 |
| WO | WO2017/196800 | 11/2017 |
| WO | WO2019/199791 | 10/2019 |
| WO | WO2019213364 | 11/2019 |

OTHER PUBLICATIONS

Bourhis, "Production Control of Residual Stresses," Glass Mechanics and Technology, Second Edition, pp. 236-243, 2014.

Mao et al., "Fabrication and characterization of 20 nm planar nanofluidic channels by glass-glass and glass-silicon bonding," www.rsc.org/loc, 8 pages, Jun. 30, 2005.

Moriceau et al., "Overview of recent direct wafer bonding advances and applications," Advances in Natural Sciences: Nanoscience and Nanotechnology, vol. 1, No. 043004, 11 pages, 2010.

Dudutis et al., Bessel beam asymmetry control for glass dicing applications, Procedia CIRP 74, pp. 333-338, 2018.

Gottmann et al., "Microcutting and Hollow 3D Microstructures in Glasses by In-Volume Selective Laser-induced Etching," Journal of Laser Micro / Nanoengineering, vol. 8, No. 1, pp. 15-18, Jan. 2013.

Jenne et al., "High-quality Tailored-edge Cleaving Using Aberration-corrected Bessel-like Beams," arXiv:2010.10226v1 [physics.optics], May 8, 2018.

Ungaro et al., "Using phase-corrected Bessel beams to cut glass substrates with a chamfered edge," Applied Optics, vol. 60, No. 3, p. 714, Dec. 10, 2020.

Decourcelle, et al., "Controlling Anisotropy," Conference Proceedings, All Eyes on Glass, Glass Performance Days, Tampere, Finland, Jun. 28-30, 2017.

Author Unknown, "Handbook for Interior Designers," 3 pages, 1998.

* cited by examiner

ELECTRONIC DEVICE ENCLOSURE INCLUDING A GLASS CERAMIC REGION

FIELD

The described embodiments relate generally to an electronic device enclosure which includes a glass ceramic region. More particularly, the present embodiments relate to electronic devices in which the glass ceramic region of the enclosure affects transmission of light to or from an optical component within the enclosure.

BACKGROUND

Many modern day portable electronic devices include cameras and various optical sensors that are integrated into the device. Typically, cameras or other optical sensors are positioned below a sheet of cover glass or plastic component of the enclosure. Embodiments described herein are directed to electronic device enclosures that include glass ceramic materials and may have advantages as compared to some traditional electronic device enclosures. The electronic device enclosures described herein generally include a glass ceramic region in the vicinity of an optical sensor or optical component, which may be specially adapted to enhance sensor performance and/or a visual appearance of the device.

SUMMARY

Embodiments described herein relate to an electronic device including an optical component and an enclosure comprising a glass ceramic region. The optical properties of the glass ceramic region and the positioning of the glass ceramic region with respect to the optical component can affect the performance of the optical component, the visual appearance of the optical component, or both. In some examples, the optical component is a sensor, a camera, or a sensor or camera module.

The enclosure may comprise a cover member and the glass ceramic region may be formed in the cover member. The glass ceramic region typically comprises crystals formed by crystallization of a glass. The optical properties of the glass ceramic region may be due to its composition and its internal structure. For example, the size of the crystals may influence the transmittance of the glass ceramic region.

In some cases, the glass ceramic region surrounds another region of the cover member which is positioned in a desired light path for the optical component. The glass ceramic region may be configured to help confine light to the desired light path, which can improve the performance of the optical component. As an example, the optical component may be configured to emit or detect light in a specified wavelength range and the glass ceramic region may be configured to have a lower transmittance for light in the specified wavelength range than the other region of the cover member. When the optical component is a sensor, the specified wavelength range may be a sensor wavelength range.

In some embodiments, the electronic device includes a sensor assembly comprising an emitter module and a receiver module and the glass ceramic region at least partially impedes optical crosstalk between the emitter module and the receiver module. The cover member may comprise a first region positioned over the emitter module and a second region positioned over the receiver module. A glass ceramic region interposed between the first region and the second region may be configured to have a lower transmittance for light in a sensor wavelength range than each of the first region and the second region. The sensor wavelength range may be a visible or infrared wavelength range.

In further cases, the glass ceramic region is positioned in a desired light path for the optical component and is configured to visually obscure at least a portion of the optical component. For example, the optical component may be configured to emit or detect infrared light and the glass ceramic region may be sufficiently infrared transmissive for operation of the optical component.

The disclosure provides an electronic device comprising a display and a reflectance sensor assembly comprising an emitter module configured to emit an optical signal and a receiver module configured to detect a reflection of the optical signal. The electronic device further comprises an enclosure enclosing the display and including a cover member positioned over the reflectance sensor assembly, the cover member comprising an emitter region configured to transmit the optical signal emitted from the emitter module, a receiver region configured to transmit the reflection of the optical signal to the receiver module, and a glass ceramic region positioned between the emitter region and the receiver region and configured to impede transmission of the optical signal.

The disclosure also provides an electronic device comprising a display and a sensor assembly including an optical emitter module configured to emit an optical signal comprising light within a sensor wavelength range and an optical receiver module configured to detect light within the sensor wavelength range. The electronic device also comprises an enclosure enclosing the display and the sensor assembly, the enclosure including a cover member including a first region positioned over the optical emitter module and having a first transmittance for light within the sensor wavelength range, a second region positioned over the optical receiver module and having a second transmittance for light within the sensor wavelength range, and a third region positioned between the optical emitter module and the optical receiver module and comprising a glass ceramic material having a third transmittance for light within the sensor wavelength range, the third transmittance less than the first transmittance and the second transmittance.

The disclosure further provides an electronic device comprising a touch sensitive display and a sensor assembly comprising an optical emitter module configured to emit an optical signal comprising light in a wavelength range and an optical receiver module configured to detect a reflection of the optical signal. The electronic device further comprises an enclosure enclosing the touch sensitive display and the optical receiver module, the enclosure including a cover member comprising an emitter region configured to transmit the optical signal, a receiver region configured to transmit the reflection of the optical signal and a glass ceramic region configured to impede transmission of the optical signal within the cover member from the emitter region to the receiver region.

In addition, the disclosure provides an electronic device comprising a display, a sensor assembly including an infrared optical module, and an enclosure enclosing the display and the sensor assembly. The enclosure includes a cover member including a glass ceramic region positioned over the infrared optical module, the glass ceramic region configured to have a first transmittance for infrared light and to have a second transmittance, less than the first transmittance, for visible light.

BRIEF DESCRIPTION OF THE DRAWINGS

The disclosure will be readily understood by the following detailed description in conjunction with the accompanying drawings, wherein like reference numerals designate like elements.

Figure 1A:
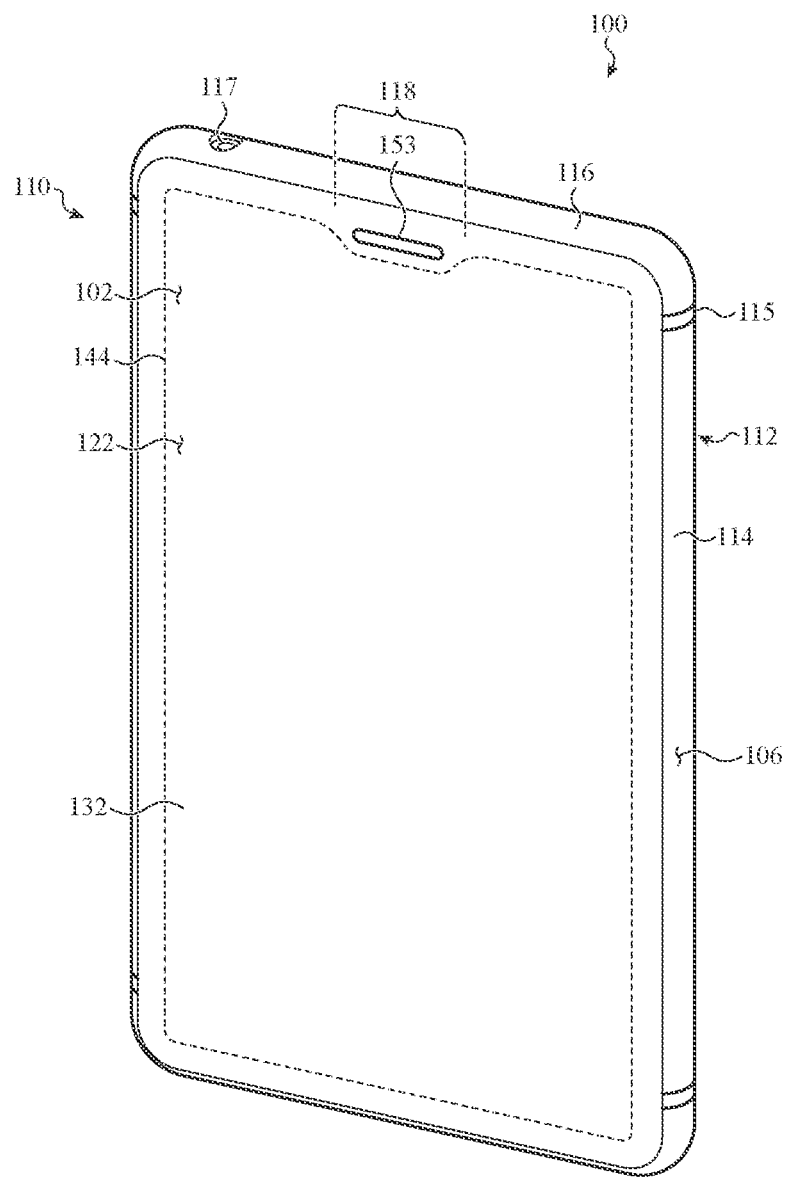
FIG. 1A shows a front view of an example electronic device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred implementation. To the contrary, the described embodiments are intended to cover alternatives, modifications, and equivalents as can be included within the spirit and scope of the disclosure and as defined by the appended claims.

Embodiments described herein relate to an electronic device including an optical component and an enclosure comprising a glass ceramic region. The optical properties of the glass ceramic region and the positioning of the glass ceramic region with respect to the optical component can affect the performance of the optical component, the visual appearance of the optical component, or both. In some examples, the optical component is sensor assembly or a camera assembly.

The enclosure may comprise a cover member and the glass ceramic region may be formed in the cover member. The glass ceramic region may have different optical or other properties as compared to another region of the cover member. For example, the other region of the cover member may be a glass region or a glass ceramic region comprising a different glass ceramic material. The glass ceramic region may also have an optical property or optical characteristic which differs from that of the other region. For example, the glass ceramic region may have a transmittance or a refractive index different from that of the other region.

The device may also include one or more optical components. As described herein, the optical component may be configured to emit or detect light in a specified wavelength range. In some cases the glass ceramic region may be configured to have a lower transmittance for light in the specified wavelength range than another region of the cover member. For example, the glass ceramic region may be configured to scatter light over the specified wavelength range. In additional cases, the glass ceramic region may be configured to have a higher transmittance for light in the specified wavelength range than for light in another wavelength range. When the optical component is a sensor, the specified wavelength range may be a sensor wavelength range.

In some cases, the glass ceramic region may be configured to help confine light to a desired light path, which can improve the performance of the optical component. For example, a first region of a cover member may be positioned in a desired light path for the optical component and second region comprising a glass ceramic material may surround the first region. If the optical component is a receiver module the first region may be a receiver region and if the optical component is an emitter module the first region may be an emitter region. If the optical component is a receiver module, the glass ceramic region may improve directional sensitivity of the optical detection. Alternately or additionally, the glass ceramic region may improve the signal to noise ratio for the receiver module by reducing the amount of ambient light reaching the sensor and/or by reducing sensor crosstalk as discussed in more detail below. If the optical component is an emitter module configured to illuminate an object outside the enclosure, more light may be directed towards the object. In some cases, the light path may form an oblique angle with respect to a thickness of the cover member, as explained in more detail with respect to FIG. 6B.

In some cases, the glass ceramic material may be configured to have a lower transmittance for light in a specified wavelength range than the first region of the cover member. For example, the glass ceramic material may scatter and/or absorb light in the specified wavelength range. In additional cases, the glass ceramic material may have a lower index of refraction than a receiver and/or emitter region of the cover member and at least some of the light emitted from the optical emitter module may be internally reflected along an interface between the receiver and/or emitter region and the glass ceramic region.

In some embodiments, the glass ceramic region at least partially impedes optical crosstalk between an emitter module and a receiver module of the electronic device. As an example, the cover member comprises a first region positioned over the emitter module, a second region positioned over the receiver module, and a third region comprising a glass ceramic material interposed between the first region and the second region. The third region may be configured to have a lower transmittance for light in a specified wavelength range than each of the first region and the second region. For example, the third region may have a third transmittance which is less than a first transmittance of the first region and a second transmittance which is less than a second transmittance of the second region. The specified wavelength range may be a visible or infrared wavelength range.

In further cases, the glass ceramic region is configured to visually obscure all or part of optical component. For example, the glass ceramic region is configured to selectively transmit light and may have a lower transmittance for visible light than for light in the wavelength range transmitted or detected by the optical component.

These and other embodiments are discussed below with reference to FIGS. 1A through 13. However, those skilled in the art will readily appreciate that the detailed description given herein with respect to these figures is for explanatory purposes only and should not be construed as limiting.

Figure 10:
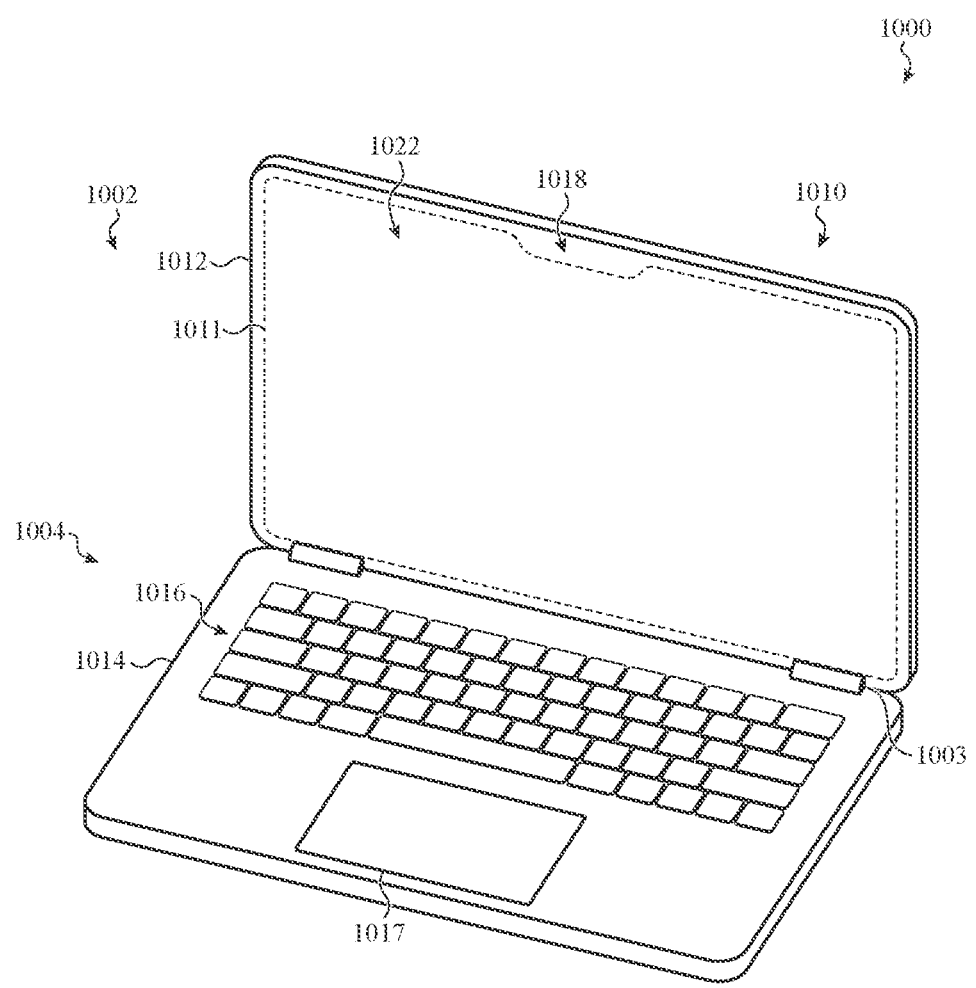
FIG. 10 shows another example of an electronic device.
Figure 11:
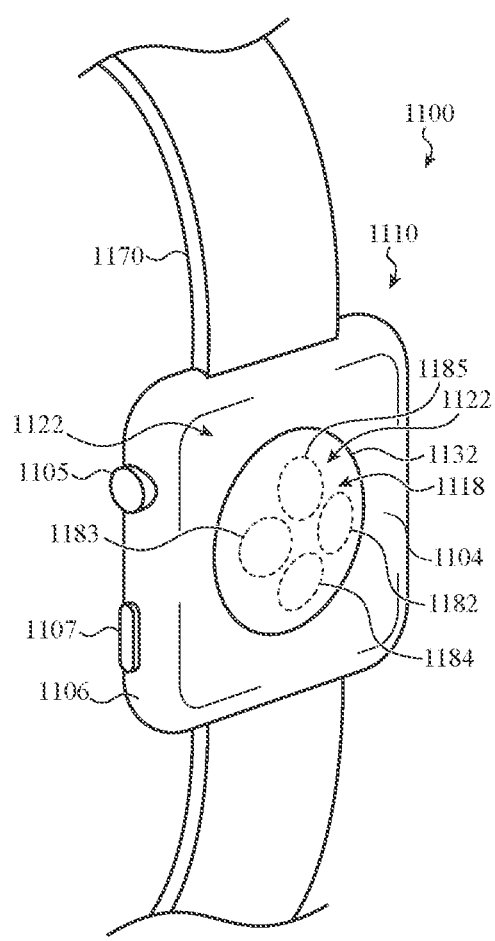
FIG. 11 shows an additional example of an electronic device.
Figure 12:
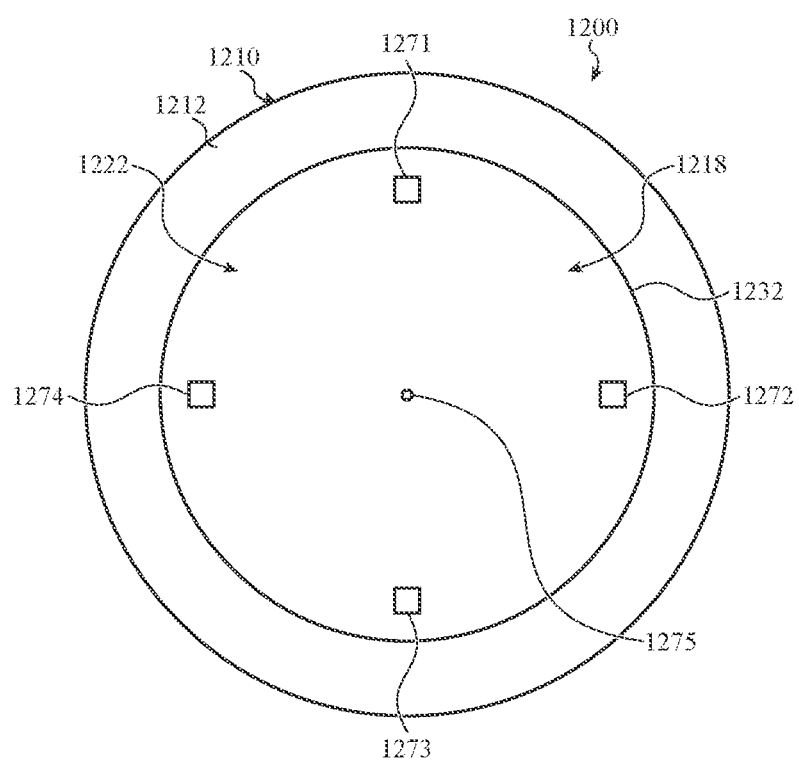
FIG. 12 shows a further example of an electronic device.

FIG. 1A shows a front perspective view of an example electronic device 100 including a cover member as described herein. The electronic device 100 may be a mobile telephone (also referred to as a mobile phone). In additional embodiments, the electronic device 100 may be a notebook computing device (e.g., a notebook or laptop as shown in FIG. 10), a tablet computing device (e.g., a tablet), a wearable device (e.g., a watch as shown in FIG. 11), a portable media player (e.g., a speaker as shown in FIG. 12) or another type of portable electronic device. The electronic device 100 may also be a desktop computer system, computer component, input device, appliance, or virtually any other type of electronic product or device component.

Figure 2:
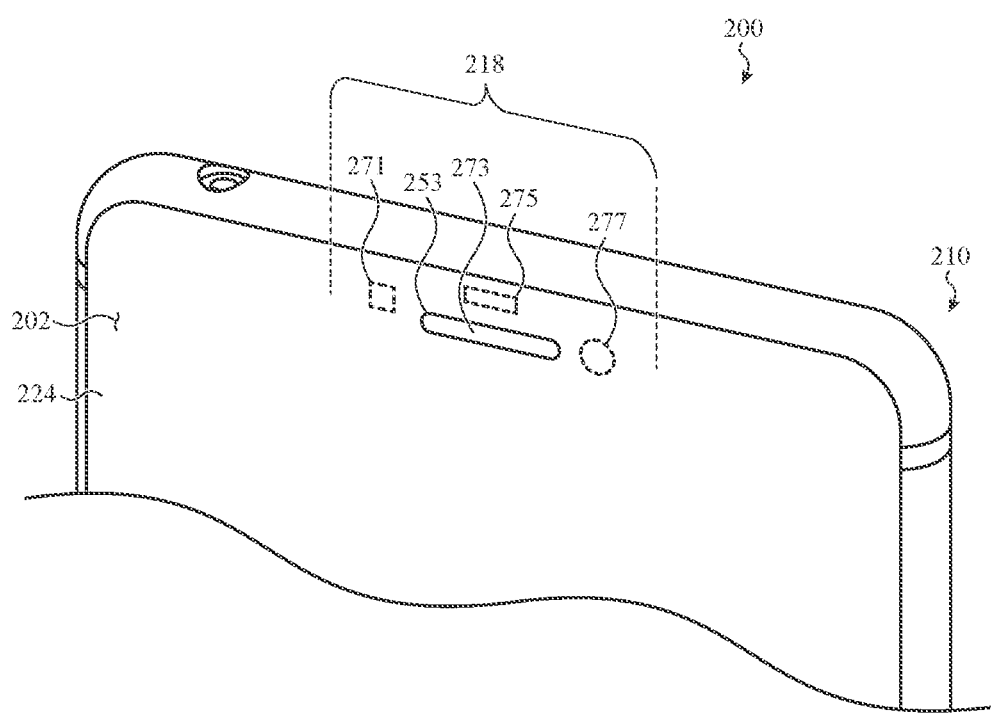
FIG. 2 shows an enlarged view of a sensor area of the electronic device of FIG. 1A.
Figure 13:
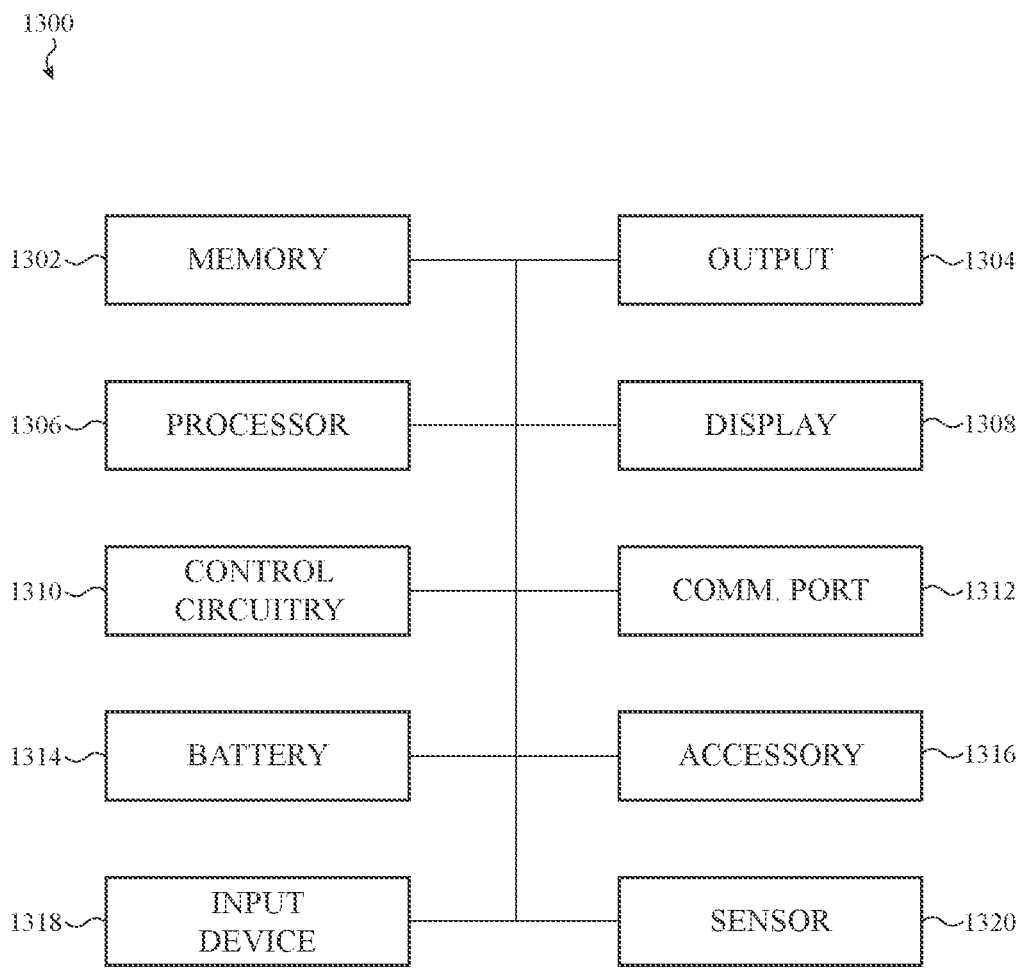
FIG. 13 shows a block diagram of components of an electronic device.

FIG. 1A schematically indicates a sensor area 118 of the electronic device 100. The electronic device 100 may include one or more sensor assemblies generally located in the vicinity of the sensor area 118. One or more camera assemblies may also be located in the vicinity of the sensor area 118. A sensor assembly may also be referred to herein simply as a sensor. Examples of sensor (assemblies) include, but are not limited to, a proximity sensor, a light sensor (e.g., an ambient light sensor), a biometric sensor (e.g., a face or fingerprint recognition sensor or a health monitoring sensor), a depth sensor, or an imaging sensor. Other types of example sensors include a microphone or a similar type of audio sensing device, a touch sensor, a force sensor, an accelerometer, a gyroscope, magnetometer, or a similar type of position/orientation sensing devices. The electronic device may further include a processing unit (also, processor) that computes a value based on a signal from the sensor. The description of sensor assemblies and processors provided with respect to FIG. 13 is generally applicable herein and, for brevity, is not repeated here. FIG. 2 provides an enlarged view of an example sensor area and additional description of camera assemblies and sensor assemblies included in the sensor area and, for brevity, that description is not repeated here.

An optical component or an optical module may include one or more light-emitting elements. An optical module including a light-emitting element may also be referred to herein as an emitter module or optical emitter module. The light-emitting element may be a light-emitting diode (LED) or a laser such as a vertical-cavity surface-emitting laser (VCSEL). Each of light-emitting elements may be configured to produce light over a specified wavelength range, such as a visible light wavelength range, an infrared (IR) light wavelength range, or an ultraviolet (UV) wavelength range. When the light-emitting element is a laser, the wavelength range may be as narrow as 1-2 nm. In some cases, an optical module may be described by the wavelength range of light emitted, such as an infrared optical module (e.g., an infrared camera module or an infrared emitter module). The light may be coherent (e.g., a laser source) or incoherent, depending on the types of sensor. The light emitted by an emitter module may be described herein as an optical signal and may include pulses of light, continuous emissions of light, discrete beams or of light, which may form a spatial pattern, or other various light emitting techniques. In some examples the optical signal is a visible light signal, an infrared light signal, or an ultraviolet light signal (also respectively referred to herein as a visible optical signal, an infrared optical signal, and an ultraviolet optical signal).

An optical component or an optical module may include a light-receiving element. An optical module including a light-receiving element may also be referred to herein as a receiver module or an optical receiver module. The light-receiving element may be a photodetector, which may include one or more photodiodes, phototransistors, or other optically sensitive elements. For example, a camera assembly may include an image sensor such as a complementary metal-oxide semiconductor (CMOS) sensor, a charge-coupled device (CCD), or other type of sensing array. The light-receiving element may be configured to detect light over the specified wavelength range of one or more light-emitting elements. In some cases, a receiver module or optical module may be described by the wavelength range of light detected, such as an infrared receiver module or an infrared optical module.

As shown in FIG. 1A, the electronic device 100 has an enclosure 110. The enclosure 110 may have a glass ceramic region as described herein. The enclosure 110 includes a cover assembly 122 and in some cases the cover assembly 122 comprises a glass ceramic region. The cover assembly 122 may at least partially define a front surface 102 of the electronic device 100. In this example the cover assembly 122 defines a substantial entirety of a front surface of the electronic device 100. The cover assembly 122 is positioned over the display 144 and may define a transparent portion (also referred to as a window region) positioned over the display 144 and configured to transmit graphical output produced by the display. The enclosure 110 may at least partially surround the display 144 and may enclose the display 144. In some cases, the display 144 is a touch sensitive display. In some cases, the enclosure 110 partially or fully encloses a sensor assembly or camera assembly.

A cover assembly such as the cover assembly 122 typically includes a cover member 132, also referred to herein simply as a member. As shown in FIG. 1A, the cover assembly 122 is a front cover assembly and the cover member 132 is a front member. In some cases, a cover assembly may be formed from multiple layers. For example, a front cover assembly may include the cover member and one or more coatings and layers such as a decorative interior layer or an anti-smudge exterior layer. In the example of FIG. 1A, the cover assembly 122 defines a hole, such as the audio port 153, to allow (audio) input or output from a device component such as a microphone or speaker.

In some cases, the cover member 122 comprises a region comprising a glass ceramic material and a region comprising a different material. In some examples, the cover member 122 is a composite cover member including or more regions comprising a glass ceramic material and one or more regions comprising a glass material. In additional examples, the cover member includes one or more regions comprising a first glass ceramic material and one or more regions comprising a second glass ceramic material, different from the first glass ceramic material. In further examples, the cover member includes one or more regions comprising a third glass ceramic material. In some cases, the glass ceramic material(s) and their respective region(s) are formed from a common precursor material, such as a crystallizable glass material or a glass ceramic material. The crystallizable glass may be regionally or locally treated (in one or more treatment steps) to create the different materials resulting in a unified or monolithic cover member comprising multiple materials, as described in more detail with respect to FIGS. 3A-3C and 7A-7C. The additional description provided with respect to FIGS. 3A-3C and 7A-7C is generally applicable herein and, for brevity, is not repeated here.

Figure 3A:
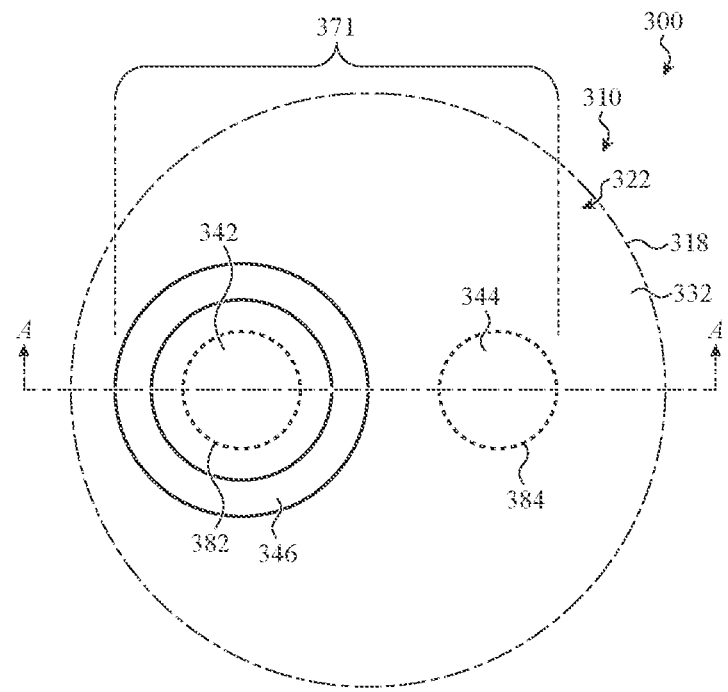
FIG. 3A shows a top view of an electronic device comprising an enclosure having a glass ceramic region.

In some cases the glass material or a glass ceramic material may be substantially transparent to visible light, infrared radiation, ultraviolet radiation, or combinations thereof. In additional cases, the glass material or the glass ceramic material may be translucent and may have a transmittance less than that of a substantially transparent region. The regions may extend from an exterior surface to an interior surface of the cover member, and thus span a thickness of the cover member. The additional description of transparent and translucent materials provided with respect to FIG. 3A is generally applicable herein and, for brevity, is not repeated here.

Figure 3B:
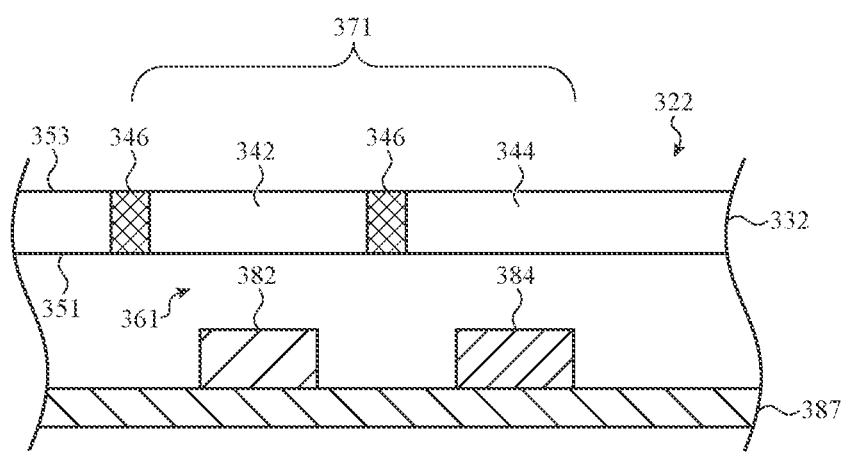
FIG. 3B shows a cross-section view of the electronic device of FIG. 3A.
Figure 3C:
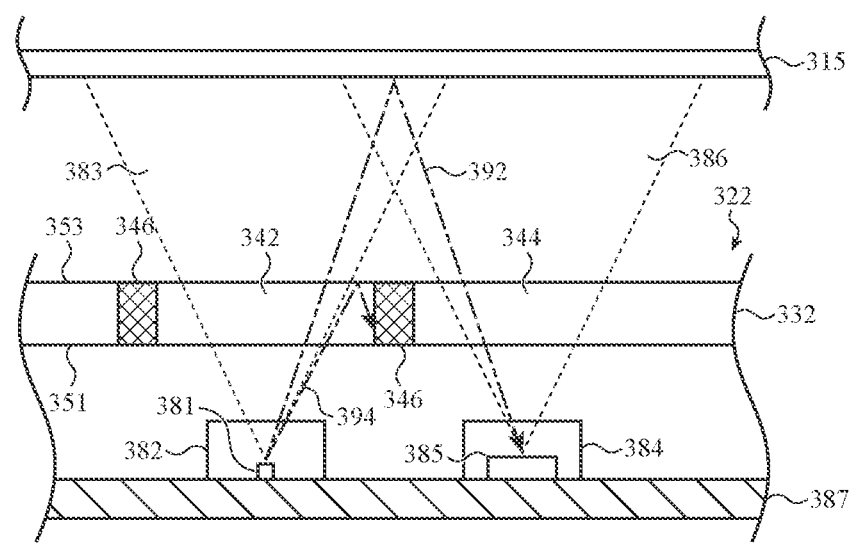
FIG. 3C is a cross-section view of the electronic device of FIG. 3A which schematically shows operation of an emitter module and a receiver module.

In some embodiments, the glass ceramic region of the cover member may be configured to reduce optical crosstalk between an emitter module and a receiver module of an optical component, as described in more detail with respect to FIG. 3C. Reducing optical crosstalk can reduce the amount of noise introduced into the receiver signal. FIGS. 3A to 6B show examples of cover members configured to reduce optical crosstalk. The description provided with respect to FIGS. 3A to 6B is generally applicable herein and, for brevity, is not repeated here.

In additional embodiments, the glass ceramic region of the cover member may be configured to obscure some or all of an optical component from view. As an example, the glass ceramic region may be configured to have a higher transmittance for infrared light than for visible light and therefore may at least partially obscure an infrared sensor assembly positioned below the glass ceramic region. In some cases, the cover member may comprise one or more interior coating layers and/or external texturing to further obscure the optical component from view, as described in more detail with respect to FIG. 7C. The additional description provided with respect to FIGS. 7A to 9B is generally applicable herein and, for brevity, is not repeated here.

In other cases, a cover member may have one or more layers of a given material which extend substantially across the width and the length of the cover member. For example, such a cover member may include one or more glass layers, glass ceramic layers, polymer layers, and/or various coatings and layers. In some cases, a cover member may be a glass cover member or a glass ceramic cover member. As an example, a cover assembly may include one or more glass layers defining a cover member and one or more coatings on the exterior surface and/or interior surface of the member.

Figure 1B:
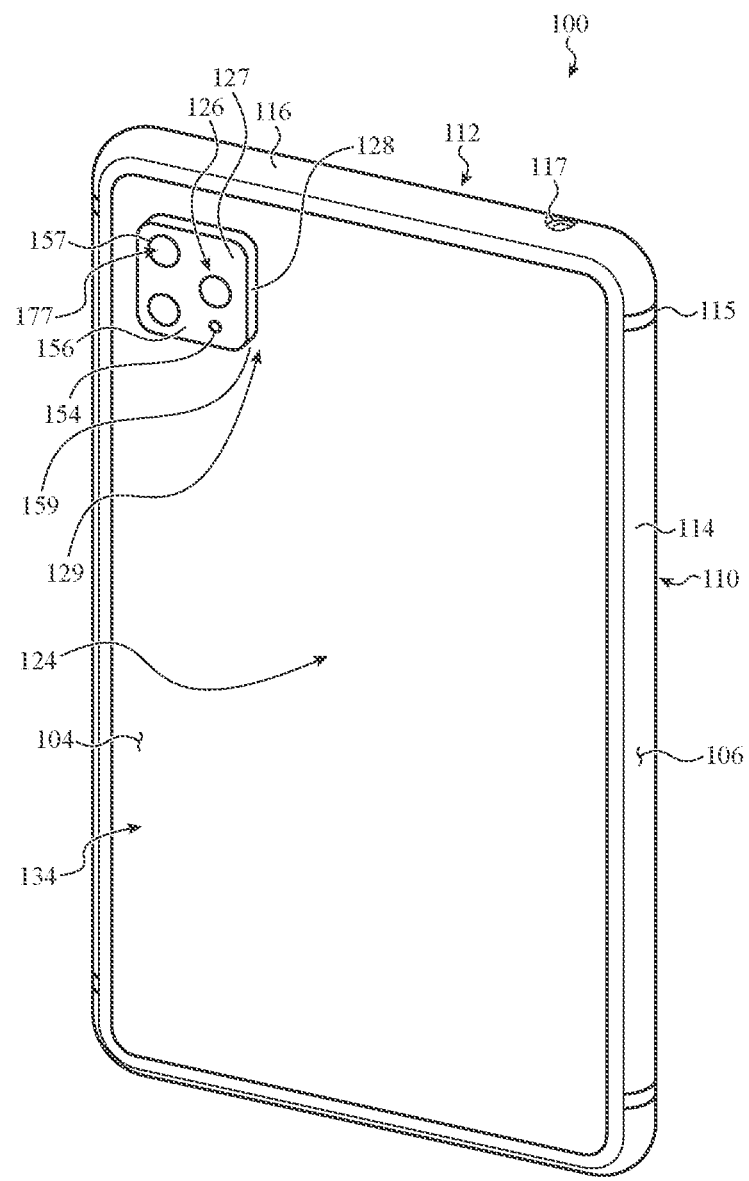
FIG. 1B shows a rear view of the electronic device of FIG. 1A.

Although the cover assembly 122 is shown in FIG. 1A as being substantially planar, the principles described herein also relate to cover assemblies and members that define a protruding feature (such as shown in FIG. 1B), a recessed feature, and/or one or more curved surfaces. In embodiments, a cover member may be three-dimensional or define a contoured profile. For example, the cover member may define a peripheral portion that is not coplanar with respect to a central portion. The peripheral portion may, for example, define a side wall of a device enclosure, while the central portion defines a front surface (which may define a transparent window or window region that overlies a display). In addition, the cover member may have a substantially uniform thickness or a thickness which varies along the cover member. For example, in some cases a thickness of a central portion of the cover member may be greater than a thickness of a peripheral portion of the cover member or vice versa.

Typical cover assemblies herein are thin, and typically have a cover member that is less than 5 mm in thickness, and more typically less than 3 mm in thickness. In some aspects, a member of a cover assembly, such as the cover members 132 and 134, can have a thickness from about 0.1 mm to 2 mm, from about 0.3 mm to 3 mm, from 0.5 mm to 2.5 mm, from 0.5 mm to 2 mm, or from 0.2 mm to 1 mm. In some cases, a member and a cover assembly including the member may have a non-uniform thickness, such as described in further detail below with respect to the cover member 134 and the rear cover assembly 124. A cover member may extend laterally across the cover assembly, such as substantially across the width and the length of the cover assembly.

As shown in FIG. 1A, the enclosure 110 further includes a housing component 112 (which may also be referred to simply as a housing). The cover assembly 122 may be coupled to the housing 112. For example, the cover assembly 122 may be coupled to the housing 112 with an adhesive, a fastener, an engagement feature, or a combination thereof.

The housing 112 may at least partially define a side surface 106 of the electronic device 100 and may include one or more metal members (e.g., one or more metal segments) or one or more glass members. In this example, the housing 112 defines all four sides or a continuous side surface of the electronic device 100. As shown in FIG. 1A, the housing 112 is formed from a series of metal segments (114, 116) that are separated by polymer or dielectric segments 115 that provide electrical isolation between adjacent metal segments. For example, a polymer segment 115 may be provided between a pair of adjacent metal segments. One or more of the metal segments (114, 116) may be coupled to internal circuitry of the electronic device 100 and may function as an antenna for sending and receiving wireless communication.

The housing 112 may define one or more openings or ports. As shown in FIG. 1A, the metal segment 116 of the housing 112 defines an opening 117. The opening 117 may allow (audio) input or output from a device component such as a microphone or speaker or may contain an electrical port or connection.

FIG. 1B shows a rear view of the electronic device 100. As shown in FIG. 1B, the enclosure 110 further includes a cover assembly 124, also referred to as a rear cover or a rear cover assembly. In some cases, the cover assembly 124 comprises a glass ceramic region as described herein. In additional cases, each of the cover assembly 122 (of FIG. 1A) and the cover assembly 124 comprises a glass ceramic region. The cover assembly 124 defines a rear surface 104 of the electronic device and the rear surface 104 defines an exterior surface of the electronic device. In the example of FIG. 1B, the cover assembly 124 defines a substantial entirety of the rear surface of the electronic device. In some cases, the electronic device 100 includes a camera assembly coupled to an interior surface of the cover assembly 124.

The cover assembly 124 includes a cover member 134. As shown in FIG. 1B, the cover assembly 124 is a rear cover assembly and the cover member 134 is a rear cover member. The cover assembly 124 may further include an exterior smudge-resistant coating, an interior cosmetic coating, or a combination thereof as previously described with respect to the front cover member 122.

As shown in FIG. 1B, the cover assembly 124 defines a feature 126 that protrudes or is offset with respect to a portion 129 of the cover assembly 124. The feature 126 may also be referred to herein as a protruding feature. The feature 126 may define a top surface 127 and a side surface 128. The portion 129 may also be referred to herein as a base portion and may define a base region of the exterior surface of the cover assembly 124. The portion 129 may be adjacent to the protruding feature and may at least partially surround the protruding feature. The feature 156 may define a textured region 156 and the base portion may define a textured region 159. The textured region 156 may have a texture that is similar or different from the textured region 159. For example, the textured region 156 may have at least one roughness parameter which is different from than that of the textured region 159.

The feature 126 may accommodate one or more device components such as an optical component 177 (e.g., a camera assembly, a proximity sensor assembly, an ambient light sensor assembly, and the like). The optical component 177 may be positioned at least partially within an opening 157 in the protruding feature. The optical component 177 may include an emitter module, a receiver module, or both. The feature 126 may also include a sensor component such a microphone which may be positioned at least partially within or below the opening 154. In implementations in which the feature 126 is used to protect one or more sensor modules or components, the feature 126 may be referred to as a sensor feature, a camera feature, a sensing panel, a camera panel, and/or a camera bump.

FIG. 2 shows an enlarged view of a sensor area of an electronic device. The electronic device 200 corresponds to the electronic device 100 of FIGS. 1A and 1B and a redundant description of shared features and components are omitted for the sake of clarity. The electronic device 200 includes a proximity sensor 271, a microphone 273, an ambient light sensor 275, and a camera assembly 277, which are generally in the vicinity of the sensor area. In the example of FIG. 2, the proximity sensor 271, the ambient light sensor 275, and the camera assembly 277 are positioned below the cover assembly 224, as schematically indicated by the dashed lines. The microphone may be positioned below the opening 253. The sensor area 218 may be located on any suitable surface 202 of the electronic device, such as a front surface or a rear surface. The cover member 224 is part of the enclosure 210.

In some cases, additional sensors may be located in the vicinity of the sensor area 218. For example, the electronic the sensor area 218 may further include a sensor assembly comprising an IR light-emitting module which projects spatial pattern (e.g., a pattern of dots), a flood IR light-emitting (illuminating) module, and an IR camera. Such a sensor assembly may be used for biometric identification. As an additional example, the sensor area 218 may include a sensor assembly that measures distance to a target, such as a LiDAR sensor assembly which is configured to illuminate an object with light and then determine the distance to the object from the reflected light (e.g., a time of flight (TOF) sensor). Such a sensor assembly may include a light emitting module (e.g., a laser) and a receiver module and may be used in combination with a camera module. A LIDAR sensor can provide a digital three dimensional representation of the object, which can be used for multiple applications, including augmented reality (AR) and virtual reality (VR). In addition, other device components, such as a speaker, may be located in and/or below the sensor area 218.

The proximity sensor 271 may comprise a light-emitting module and a light-receiving module, as shown in the detail view of FIGS. 3A to 3C. The light emitting module of a proximity sensor may produce infrared light. In some embodiments, the light emitting module produces near-infrared light such as light having a wavelength from about 800 nm to about 2.5 microns, from 900 nm to about 1.6 microns, or from about 800 nm to about 1000 nm. In some cases, the proximity sensor may be a time of flight sensor.

The ambient light sensor 275 may comprise a light sensing module which can provide measurements of ambient light intensity. In some cases, the ambient light sensor can include color sensing. Although the example of FIG. 2 shows an ambient light sensor 275 as separated from the proximity sensor 271, in other examples the ambient light sensor 275 may be packaged with the proximity sensor 271.

The camera assembly 277 typically includes a camera module. The camera module of the camera assembly 277 may produce images from visible light. However, the electronic device 200 may also include camera modules and camera assemblies which produce images from infrared light. In some cases, a camera module includes an optical sensing array and/or an optical component such as a lens, filter, or window. In additional cases, a camera module includes an optical sensing array, an optical component, and a camera module housing surrounding the optical sensing array and the optical components. The camera module may also include a lens assembly, which may include moving elements and/or moving lenses. For example, a focusing assembly may include an actuator for moving a lens of the camera module. In some cases, the optical sensing array may be a complementary metal-oxide semiconductor (CMOS) array or the like.

FIG. 3A shows a top view of an electronic device 300 comprising an enclosure 310 having a glass ceramic region. The electronic device 300 includes a sensor 371 positioned below a cover assembly 322 and comprising an emitter module 382 and a receiver module 384. The cover assembly 322 includes a cover member 332 comprising a first region 342, a second region 344 and a third region 346. The emitter module 382 and the receiver module 384 are located in a sensor area 318 of the cover assembly and are schematically illustrated with dashed lines in FIG. 3A. In some cases, the first region 342 and the second region 344 may be positioned along a side of a window region of the cover member 332.

As shown in FIGS. 3A to 3C, the emitter module 382 is positioned below the first region 342 (also referred to herein as an emitter region) and the receiver module 384 is positioned below the second region 344 (also referred to herein as a detector region). The first region 342 may be configured to transmit (emitted or outbound) light from the emitter module through a first thickness of the cover member and the second region 344 may be configured to transmit (received or inbound) light to the receiver module through a second thickness of the cover member. The cover member 332 defines an exterior surface 353 and an interior surface 351.

The third region 346 is interposed between the first region 342 and the second region 344 and comprises a glass ceramic material. In the example of FIGS. 3A to 3C, the third region is adjacent each of the first region 342 and the second region 344. In some cases, the glass ceramic material is capable of at least partially optically isolating the receiver module 384 from the emitter module 382 and impeding optical crosstalk between the emitter module 382 and the receiver module 384 as discussed in further detail below with respect to FIG. 3C.

In the example of FIGS. 3A to 3C, the third region 346 includes a glass ceramic material which has at least one optical property, such as a transmittance, different than the first region 342 and the second region 344. The glass ceramic material of the third region 346 typically differs in internal structure from the material(s) of the first region 342 and the second region 344. The first region 342, the second region 344, and the third region 346 may be integrally formed, as described in greater detail below.

FIG. 3B shows a cross section view of the electronic device 300 along A-A and FIG. 3C is an additional cross-section view which schematically shows operation of the emitter module and the receiver module of FIG. 3B. In some cases, the sensor 371 may be configured to operate in a reflective sensing mode and the sensor 371 is therefore a reflectance sensor. For example, light from the emitter module 382 (e.g., an optical signal) may be transmitted through the cover assembly 322 to an object and light reflected from the object (e.g., the optical signal reflected from the object) may be detected by the receiver module 384, as schematically shown in FIG. 3C. In some cases, the receiver module 384 may receive only a portion of the light produced by the emitter module 382 (e.g., a first portion of the light).

In the example of FIGS. 3A to 3C, the third region 346 has at least one optical property, such as a transmittance, different than the first region 342 (the emitter region) and the second region 344 (the receiver region). In some cases, the glass ceramic material of the third region 346 may be configured to at least partially impede a "short cut" for transmission of light from the emitter module 382 to the receiver module 384 as described in more detail with respect to FIG. 3C below. For example, the glass ceramic material of the third region may be configured to impede transmission of another portion of the light produced by the emitter module 382 which is directed towards and/or enters the third region instead of exiting the cover assembly 322 (e.g., a second portion of the light). The light transmission properties of the third region 346 can therefore allow closer spacing of the emitter and the receiver.

Figure 5A:
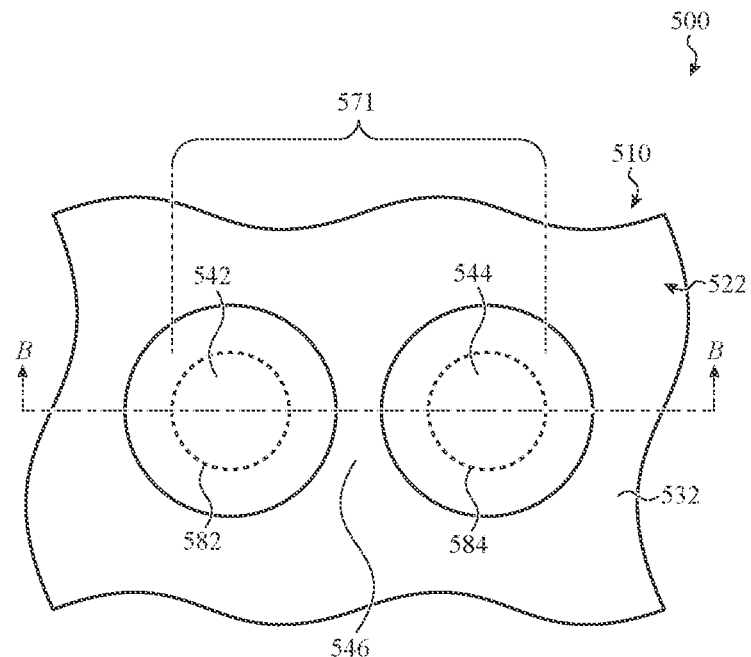
FIG. 5A shows a top view of an additional electronic device comprising an enclosure having a glass ceramic region.
Figure 5B:
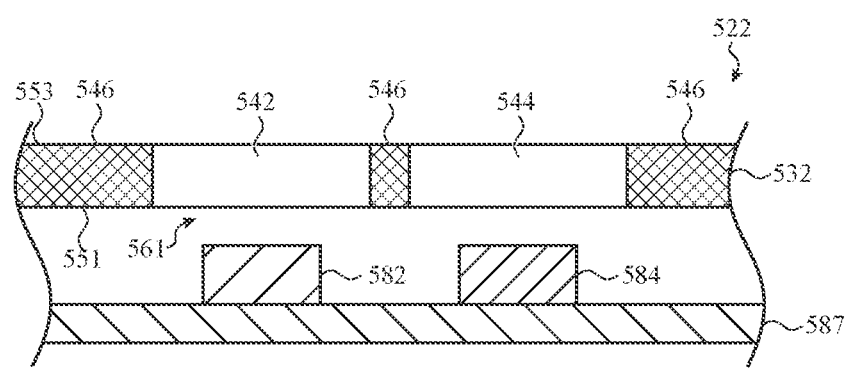
FIG. 5B shows a cross-section view of the electronic device of FIG. 5A.

In the example of FIGS. 3A and 3B, the third region 346 forms a ring or other optical barrier around the first region 342. It should be understood that this example is not limiting and that the third region 346 may be interposed between the first and second regions (342, 344) in a variety of ways. As examples, the third region may form a ring or other suitable shape surrounding the first region 342 (the emitter region), the second region 344 (the receiver region), or both (as shown in FIGS. 5A and 5B). In some cases, a lateral dimension of the third region may be from 100 microns to 1 cm, from 250 microns to 5 mm, from 250 microns to 1 m, or from 500 microns to 5 mm.

The emitter module 382 may be configured to emit light over a specified wavelength range, such as a visible light wavelength range, an infrared (IR) light wavelength range, or an ultraviolet (UV) wavelength range. The light may be emitted from the emitter module in continuous form or as one or more pulses. The receiver module 384 may be configured to detect light over the specified wavelength range. The visible light range may be associated with a spectral color. For example, a violet color may be associated with light having a wavelength from about 380 nm to about 450 nm, a blue color may be associated with light having a wavelength between about 450 nm to about 495 nm, a cyan color may be associated with light having a wavelength from about 490 nm to about 520 nm, a green color may be associated with light having a wavelength between 495 nm and 570 nm, a yellow color may be associated with light having a wavelength from about 570 nm to about 590 nm, an orange color may be associated with light having a wavelength from about 590 nm to 620 nm, and a red color may be associated with light having a wavelength from about 620 nm to about 750 nm. The IR range may be a near-IR range, such as from about 800 nm to about 2.5 microns, from about 900 nm to about 1.6 microns, or from about 800 nm to about 1000 nm.

As shown in FIG. 3B, the emitter module 382 and the receiver module 384 may be spaced apart from the cover assembly 322 by a gap 361. The size of the gap 361 has been exaggerated in FIGS. 3B and 3C to more conveniently illustrate light paths. In addition, the emitter module 382 and the receiver module 384 may be supported by a support 387, which may include a circuit substrate or other supporting structure. It should be understood that the form of the support 387 is not limiting and that the sensor 371 may include additional elements not shown in FIG. 3B, such as circuitry and additional packaging for the emitter and receiver modules.

The shape of the emitter module 382 and of the receiver module 384 are not limited to the shapes shown in the example of FIGS. 3A and 3B, but can be any suitable shape, including a rectangular prism, a cube, or a cylinder. The electronic device 300 may be an example of the electronic device 100 or of any other electronic device described herein. The sensor area 318 may be located on any suitable surface of the electronic device, such as a front surface or a rear surface.

FIG. 3C schematically shows operation of the emitter module 382 and the receiver module 384. The emitter module 382 includes an emitter element 381 which emits light toward the cover assembly 322. At least a portion of the light is transmitted through the cover member 332 and the cover assembly 322. The dashed lines schematically indicate a desired path for light produced by the emitter element 381 and received by the receiver element 385. The emitter module 382 has a field of view 383. The receiver module 384 has a field of view 386 and includes a receiver element 385. In examples where the field of view 386 of the receiver module is wider than a width of the second region 344 (the receiver region) and the third region 342 may help block stray light (e.g. ambient light) from reaching the receiver module.

An example optical signal typically includes multiple rays and/or beams of light. By way of example, the light ray 392 is transmitted through the cover member 332 and the cover assembly 322, is within the field of view 383, is reflected from the object 315, and is received by the receiver element 385. Therefore, detection of light ray 392 by the receiver element 385 can provide information about the object 315. The desired path of light emitted by the emitter module 382 passes through first region 342 and the desired path of light transmitted towards the receiver module 384 passes through the second region 344.

In contrast, the light ray 394 does not pass through the exterior surface 353 of the cover member 332 and therefore cannot provide information about the object 315. Light which reaches the receiver element 385 without being reflected by the object 315 is referred to herein as creating "optical crosstalk" between the emitting module 382 and the receiving module 384. In the example of FIG. 3C, when the light ray 394 enters the cover member 332 it is internally reflected from the exterior surface 353 of the cover member 332. If the third region 346 does not impede the propagation of the light ray 394 towards the receiving element 385 (within the cover member 332), the light ray 394 may reach the receiving element 385 of the receiver module 384 after undergoing one or more internal reflections within the cover member 332. A path allowing light to reach the receiving element 385 without being reflected from an object external to the electronic device is referred to herein as a "short cut." The light ray 394 is outside the desired path indicated by the dashed lines.

As shown in FIG. 3C, the third region 346 impedes propagation of the light ray 394 toward the receiver element 385 within the cover member 332. More generally, the third region 346 of the cover member 332 is configured to at least partially impede the propagation of light (e.g., an optical signal) from the emitter module through the third region. For example, the third region 346 may be configured to at least partially impede propagation of light towards the second region 344. As explained in more detail below, the glass ceramic material of the third region 346 may impede the propagation of light by scattering, absorption, and/or reflection. The third region may therefore at least partially optically isolate the second region 344 from the first region 342.

The ability of the third region 346 to at least partially impede the propagation of light in a given direction may be measured in several ways. For example, the transmittance of the third region 346 (or of a specified thickness of the third region) over a specified wavelength range can be used as one measure. The transmittance can be measured as the total transmittance, the direct transmittance (also referred to as regular transmittance), the diffuse transmittance, or combinations thereof. In some cases, the transmittance of the third region 346 is less than a transmittance of each of the first region 342 and the second region 344. For example, the transmittance of the third region 346 may be less than or equal to 50%, less than or equal to 40%, less than or equal to 30%, or less than or equal to 20%. The transmittance of each of the first region 342 and the second region 344 may be at least 60%, at least 70%, at least 80%, at least 85%, at least 90%, or at least 95%. For the example of FIGS. 3A to 3C, these transmittance values may be referenced to the specified wavelength range for the emitter module 382 or a subset of this wavelength range.

In some cases, an internal structure of the third region 346 may be configured to at least partially impede the propagation of light (over a specified wavelength range) towards the second region 344. The first region 342 (positioned over the emitter module 382) and the second region 344 (positioned over the receiver module 384) of the cover member 332 may have an internal structure configured to transmit the light to a greater extent than the third region 346. The internal structure of the third region, when implemented over a large enough region, may also improve the strength of the cover member and/or help to arrest crack propagation in addition to providing the optical benefits described herein. The internal structure of a region of the cover member may be characterized at least in part by one or more phase(s) present in the region, a characteristic length scale of the phase(s) (e.g., a size of a crystalline phase present in the region), and a characteristic amount of the one or more phase(s). The internal structure may also be referred to as a microstructure or a nanostructure (when the characteristic length scale is from about 1 nm to about 100 nm).

Typically, the third region 346 comprises a glass ceramic material, also referred to herein simply as a glass ceramic. As referred to herein, a glass ceramic material comprises one or more crystalline phases formed by crystallization of a (precursor) glass material. Therefore, the glass ceramic is at least partially crystallized. The glass ceramic may further comprise an amorphous (glass) phase and the crystals may be dispersed over the third region. This glass phase may be a residual phase remaining after crystallization. The crystalline phases may form particles (also referred to herein as crystals). In some cases, a crystal may comprise multiple crystallites. For example, a crystal may comprise multiple crystallites of a single phase. A crystal may further comprise crystallites of different phases. For example, a crystal may comprise a crystallite of a nucleating phase (e.g., $TiO_2$, $ZrO_2$) in addition to one or more crystallites of another phase (e.g., a later crystallizing phase in the glass ceramic). The size of the crystals (or crystallites if the crystal comprises distinct crystallites) may be measured through x-ray diffraction and/or microscopy, such as transmission electron microscopy. In some examples, the crystalline phase in the third region 346 comprises from 20% to 90%, from 30% to 90%, from 40% to 90%, from 50% to 90%, from 60% to 90%, from 70% to 90%, from 75% to 95%, or greater than 80% of the at least partially crystallized glass ceramic by volume. This volume percentage may be averaged over the region.

Figure 4:
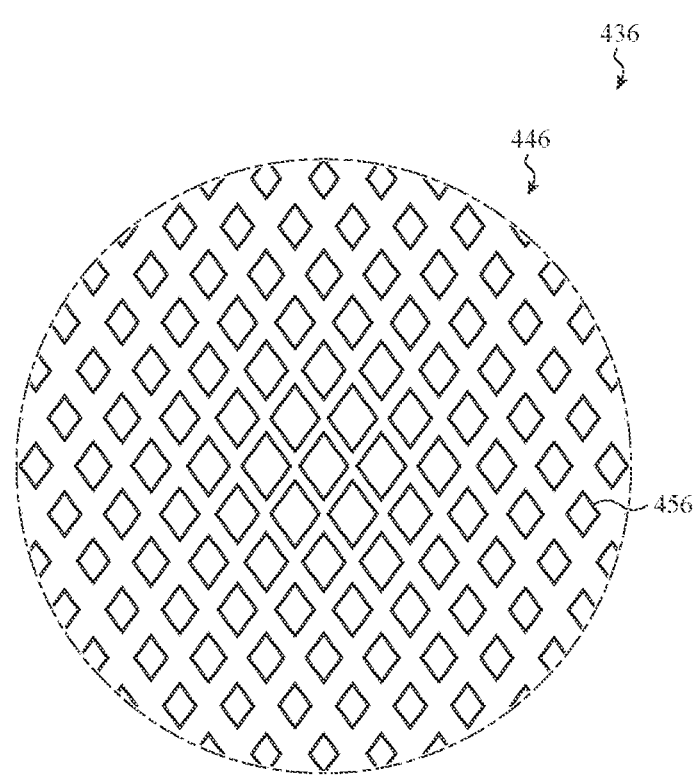
FIG. 4 schematically shows a detail view of a glass ceramic region.

In some cases the glass ceramic material of the third region 346 at least partially impedes propagation of light by scattering. For example, at least some of the crystals in the third region 346 may have a size which scatters light over all or part of the wavelength range produced by the emitter module 382. For Mie scattering, the size of a crystal may determine whether or not a given wavelength of light would be scattered. In some cases longer wavelengths of light may be scattered by larger crystals, but may not be scattered by smaller crystals. For example, at least some of the crystals in the third region 346 may have a size (e.g., diameter) which is a multiplier of a wavelength of the light. For example, this multiplier may be from 0.06 to 1.0, from 0.1 to 0.7, from 0.1 to 0.3, or from 0.3 to 1.0. The size of the crystals may be controlled so that at least some of light is scattered backwards and to the side (relative to the incoming direction of the light) to more effectively impede the light. In some cases, the third region 346 may include a distribution of crystal sizes, as schematically illustrated in FIG. 4. Therefore, the median crystal size in the third region 346 may be less than the size obtained using the multipliers listed above.

In some cases the median crystal size for at least partially impeding propagation of near-IR light may be from about 50 nm to about 2 microns, from about 75 nm to about 1 micron or from about 100 nm to about 1.6 microns. These crystal sizes may also at least partially impede transmission of visible light. In some cases the median crystal size for at least partially impeding propagation of visible light is from about 30 nm to about 780 nm, from about 50 nm to about 550 nm, from about 50 nm to about 230 nm, or from about 230 nm to about 780 nm.

FIG. 4 schematically shows a detail view of a glass ceramic region 446 of a cover member 436. The glass ceramic region 446 includes multiple crystals 456. In the example of FIG. 4, the crystals 456 have a distribution of sizes. For example, the size of the crystals may be generally smaller at a periphery of the third region 446, which is adjacent to another region. The size of the crystals 456 is generally larger in a central portion of the third region 346, resulting in a gradient in crystal size. Although the crystals 456 shown in FIG. 4 have a regular shape, this example is not limiting and the crystals may have an irregular shape. In addition, the shape of the crystals may be spherical, faceted, elongated, layered, or any other suitable shape.

The glass ceramic material of the third region 346 may alternately or additionally at least partially impede propagation of light by reflection and/or absorption. For example, if the refractive index of the third region is lower than that of the first region, light may be at least partially reflected along an interface between the third region and the first region. The magnitude of the difference in the refractive index between the third region and the first region may at least partially depend on the difference between the refractive index of the crystals and the refractive index of the glass from which the crystals were formed. In addition, if the crystals are much larger than the wavelength of light (such as about 500 times the wavelength of light), light may reflect from individual crystals. As a further example, in some cases the third region may include absorption centers which selectively absorb the light entering the third region. The glass ceramic material of such a third region may include one or more metals or metal oxides which contribute to the formation of the absorption center. The presence of these absorption centers may give the third region a colored appearance.

As previously mentioned, the first region 342 (positioned over the emitter module 382) and the second region 344 (positioned over the receiver module 384) may have an internal structure configured to provide a higher transmittance to light over the specified wavelength range than the third region 346. In some cases, each of the first region 342 and the second region 344 is a glass region. The first region 342 may be a first glass region and the second region 344 may be a second glass region. The first glass region and the second glass region may have substantially the same composition and structure.

In additional cases, each of the first region 342 and the second region 344 comprises nuclei for crystallization dispersed in a crystallizable glass. The first region 342 and the second region 344 may be substantially free of a crystalline phase formed from the principal elements of the glass ceramic (also referred to as a principal crystalline phase) or only a small amount of the principal crystalline phase may be present in these regions. For example, a nucleus may be a crystallite of a titanium oxide (e.g., $TiO_2$), a zirconium oxide ($ZrO_2$), or a mixed oxide of titanium and zirconium. The nucleus may be from about 2 nm to about 6 nm in size. The first region 342 and the second region 344 may have substantially the same composition and structure.

In additional cases, each of the first region 342 and the second region 344 is a glass ceramic region different from the glass ceramic third region 346. For example, the glass ceramic material of the third region 346 may have a larger median crystal size than a glass ceramic material of each of the first and second regions 342 and 344. The first region 342 may be a first glass ceramic region and the second region 344 may be a second glass ceramic region. The first glass ceramic region 342 and the second glass ceramic region 344 may have substantially the same composition and structure.

In some cases, each of the first glass ceramic region and the second glass ceramic region is substantially transparent. For example, each of the first glass ceramic region and the second glass ceramic region may have a transmittance of at least 70%, 80%, 85%, 90%, or 95% over the a visible wavelength range (e.g., the visible spectrum). The first glass ceramic region and the second glass ceramic region may have a similar transmittance over an infrared sensor range. The median crystal size of the first glass ceramic region and the second glass ceramic region may be less than or equal to 50 nm, such as from 5 nm to 30 nm, or from 10 to 50 nm.

In additional cases, each of the first glass ceramic region and the second glass ceramic region has a greater transmittance for light within a sensor wavelength range than for visible light. As a result, the first region 342 may at least partially obscure the emitter module 382 and the second region 344 may at least partially obscure the receiver module 384 from view by a user. For example, the first region 342 and the second region 344 may have a size which scatters light over all or part of the visible spectrum, but scatters light of longer wavelengths to a lesser extent. For example, near-IR wavelengths of light, such from about 800 nm to about 2.5 microns from 900 nm to about 1.6 microns, or from about 800 nm to about 1000 nm, may be scattered to a lesser extent than visible light wavelengths (in a visible spectrum from about 380 nm to about 740 nm). As a particular example, the crystals in first region 342 and the second region 344 may be sized to scatter light in the visible spectrum though Mie scattering, but may be sized to scatter light in a near-IR wavelength range to a lesser extent through Mie scattering. In some cases, the first region 342 and the second region 344 may predominantly include crystals having a size (e.g., a diameter) which is less than or equal to a multiplier of a near-IR wavelength of light, such a multiplier of about 0.06 or 0.1. In addition, at least some of the crystals in first region 342 and the second region 344 may have a size (e.g., a diameter) which is greater than or equal to a multiplier of a visible light wavelength, such a multiplier of about 0.1 or 0.3. For example, a median crystal size of the first region 342 and the second region 344 may be from about 30 nm to about 80 nm, from about 50 nm to about 100 nm, or from about 90 nm to about 150 nm.

Alternately or additionally, the glass ceramic material of the third region 346 may have at least one crystalline phase that differs from the crystalline phase(s) in the glass ceramic material(s) of the first and second region 342, 344, as explained in more detail below. Furthermore, in some cases the first region 342 may be a glass region and the second region 344 may be a glass ceramic region or vice versa.

A cover member comprising a glass ceramic third region 346 different from the first and second regions (342,346) can be formed by locally modifying a precursor of the cover member to form the third region. A precursor of the cover member may also be referred to herein as a precursor member. When the precursor member is formed of a single piece of material the resulting cover member is also integrally formed. The cover member may have substantially the same shape as the precursor member, but has been locally modified to have an internal structure (e.g., a microstructure or a nanostructure) which differs from that of the precursor member.

The precursor member may be locally modified by locally applying energy to at least one region of the precursor member. For example, the at least one region of the precursor member may be locally heated with a laser or other localized source of heat. In addition, the precursor member may be heated in a furnace, oven, or the like while the regions which are not to be locally modified are cooled or otherwise shielded from heat. In further examples, the at least one region of the precursor member may be exposed to ultraviolet radiation, an electron beam, or the like.

In some cases, the precursor member comprises a crystallizable glass and the local modification of the precursor comprises locally forming crystals in a crystallizable glass member. When the precursor comprises a crystallizable glass, locally forming crystals may comprise locally forming nuclei for crystallization and then growing the crystals at some or all of the nuclei. The operation of forming nuclei for crystallization may be conducted at a lower temperature (e.g., a nucleation temperature) than the operation of growing the crystals at some of all of the nuclei (e.g., a crystallization temperature). The first and second regions may remain substantially uncrystallized. For example, a volume percentage of crystals in the first and second regions may be less than 10%, less than 5%, or less than 2%. This volume percentage may be averaged over the region.

In further cases, the precursor member comprises nuclei for crystallization (e.g., nuclei formed wholly or in part from one or more nucleating agents) dispersed in a crystallizable glass. The precursor member may be substantially free of a crystalline phase formed from the principal elements of the glass ceramic (also referred to as a principal crystalline phase) or only a small amount of the principal crystalline phase may be present in the precursor. For example, a nucleus may be formed wholly or in part of one or more crystallites of a titanium oxide (e.g., $TiO_2$), a zirconium oxide ($ZrO_2$), or a mixed oxide of titanium and zirconium. A nucleus may have a size that is small relative to typical crystal sizes of a principal crystalline phase. The volume density of the nuclei may be smaller than typical volume densities of the principal crystalline phase. For example, the nucleus may be from about 2 nm to about 6 nm in size.

In additional cases, the precursor member comprises a glass ceramic comprising a crystalline phase and local modification of the precursor member comprises locally growing crystals of the same crystalline phase, locally forming crystals of a different crystalline phase, or combinations thereof. Therefore, local modification produces a glass ceramic material which is different from the glass ceramic material of the precursor member. As examples, the crystalline phase in the precursor member comprises from 20% to 90%, from 30% to 90%, from 40% to 90%, from 50% to 90%, from 60% to 90%, from 70% to 90%, from 75% to 95%, or greater than 80% of the at least partially crystallized glass ceramic by volume. This volume percentage may be averaged over a region of the precursor member.

When the cover member 332 is produced by local modification of a glass ceramic precursor member, the glass ceramic material of the third region 346 is different from the glass ceramic material of the first region 342 and the second region 344. When the internal structure of the precursor member allows enlargement of the size of the crystals, the glass ceramic material of the third region 346 may have a larger median crystal size than the glass ceramic material of each of the first and second regions 342 and 344. Alternately or additionally, the glass ceramic material of the third region 346 may have at least one crystalline phase that differs from the crystalline phase(s) in the glass ceramic material of the first and second regions 342 and 344. For example, if a region of the glass ceramic precursor member is locally heated to a higher temperature and/or for a longer time than used to form the crystalline phase(s) in precursor member, a different crystalline phase may form in the locally heated region.

In some cases, the size of the crystals may vary across the third region 346 as schematically shown in FIG. 4. For example, the size of the crystals may be generally smaller at a periphery of the third region 346 (adjacent to the first region 342 and/or the second region 344) and generally larger in a central portion of the third region 346, resulting in a gradient in crystal size. The gradient in crystal size may result from a variation in the energy applied to a region of the precursor member during local modification of the precursor member. For example, a gradient in crystal size may result from a thermal gradient across the region of the precursor member. The gradient in crystal size may make the boundary of the third region less visually distinct or perceptible to the user.

The precursor member may be a glass ceramic precursor member and cover member after the local modification may be a glass ceramic cover member. The amorphous phase and the crystalline phase together may comprise 90% to 100% of the volume of the glass ceramic cover member. In some cases, the cover member includes a sufficiently high volume percentage of the crystalline phase to be described as a glass ceramic cover member. For example, a glass ceramic cover member may include from 50% to 90%, from 60% to 90%, from 70% to 90%, from 75% to 95%, or greater than 80% of the crystalline phase by volume.

By the way of example, the glass ceramic material may be an alkaline silicate, an alkaline earth silicate, an aluminosilicate, a boroaluminosilicate, a perovskite-type glass ceramic, a silicophosphate, an iron silicate, a fluorosilicate, a phosphate, or a glass ceramic material from another glass ceramic composition system. In some embodiments, the glass ceramic portion comprises an aluminosilicate glass ceramic or a boroaluminosilicate glass ceramic. In addition to the principal elements of the glass ceramic material (e.g., aluminum, silicon, and oxygen for an aluminosilicate) the glass ceramic material may also include other elements. For example, the glass ceramic material (and the precursor glass) may include elements used to nucleate crystalline phases of the glass ceramic material, such as titanium oxide, a zirconium oxide, or combinations thereof. Aluminosilicate and boroaluminosilicate glass ceramics may further include monovalent or divalent ions which compensate charges due to introduction of aluminum ions in the glass ceramic. For example, an alkali aluminosilicate may include alkali metal ions which compensate for the inclusion of aluminum ions in the glass ceramic.

A lithium aluminosilicate (LAS) glass ceramic may be formed from a lithium aluminosilicate glass. For example, the lithium aluminosilicate glass may comprise from 60 wt % to 90 wt % $SiO_2$, from 5 wt % to 30 wt % $Al_2O_3$, and from 2 wt % to 15 wt % $Li_2O$. The lithium aluminosilicate glass may also comprise a relatively small amount (e.g., a few percent by weight) of a nucleating agent such as $TiO_2$, $ZrO_2$, $SnO_2$, $Ta_2O_5$, $Ta_2O_5$, or combinations thereof. The lithium aluminosilicate glass may also comprise a relatively small amount of one or more alkaline earth oxides or one or more alkali metal oxides other than lithium oxide. Lithium aluminosilicate glasses can form several types of crystalline phases, including β quartz solid solution crystals, keatite solid solution crystals (β spodumene solid solution crystals), petalite crystals, and lithium disilicate crystals. Some of these crystalline phases can be transformed into other crystalline phases. For example, β quartz solid solution crystals can transform into keatite/β spodumene crystals. As an additional example, mixtures of crystal phases can be transformed into different mixtures, such as transformation of a mixture including lithium disilicate and petalite crystals into a mixture including lithium disilicate and β spodumene solid solution crystals. In some cases, the crystals may have a coefficient of thermal expansion which is close to zero or even less than zero.

The cover member may be chemically strengthened by one or more ion exchange operations. During each ion exchange operation, ions present in the cover member can be exchanged for larger ions in an ion-exchanged zone extending from a surface of the cover member. A compressive stress layer extending from a surface of the cover member may be formed in the ion-exchanged zone. In some cases, the ion-exchanged zone is formed in one or more glass materials of the cover member. For example, an ion exchanged zone may be formed in a glass material of a glass region, in the glass material of a region comprising crystallization nuclei dispersed in a glass material, and/or in the residual glass material of a glass ceramic region.

For example, an ion-exchangeable glass material of the cover member may include monovalent or divalent ions such as alkali metal ions (e.g., $Li^+$, $Na^+$, or $K^+$) or alkaline earth ions (e.g., $Ca^{2+}$ or $Mg^{2+}$) that may be exchanged for other alkali metal or alkaline earth ions. If the glass material comprises sodium ions, the sodium ions may be exchanged for potassium ions. Similarly, if the glass material comprises lithium ions, the lithium ions may be exchanged for sodium ions and/or potassium ions.

In an example, the chemical strengthening process involves exposing the cover member to a medium containing the larger ion, such as by immersing the cover member in a bath containing the larger ion or by spraying or coating the cover member with a source of the larger ions. For example, a salt bath comprising larger ions (e.g., a bath containing potassium ions or a mixture of potassium ions and sodium ions) may be used for ion exchange. Suitable temperatures for ion exchange are above room temperature and are selected depending on process requirements. The ion exchange process may be conducted at a temperature below the strain point of the glass material. The member may be cooled following the ion exchange operation. Depending on the factors already discussed above, a compressive stress layer as deep as about 10 to 250 microns can be formed in a glass region. The surface compressive stress (CS) may be from about 300 MPa to about 1100 MPa. A mask can be used to shield portions of the cover member from ion exchange as desired. Optionally, the member is washed after the ion exchange operation.

FIG. 5A shows a top view of an electronic device comprising an enclosure 510 having a glass ceramic region. The electronic device 500 includes a cover member 522 including a first region 542, a second region 544 and a third region 546. The sensor 571 includes an emitter module 582 positioned below the first region 542 and a receiver module 584 positioned below the second region 542. The third region 546 includes a glass ceramic material capable of at least partially optically isolating the receiver module 584 from the emitter module 582 as previously discussed with respect to FIG. 3C. The description of the sensor 371 is applicable to the sensor 571 and, for brevity, is not repeated here. FIG. 5B shows a cross section view of the electronic device 500 along B-B. The electronic device 500 may be an example of the electronic device 100 or of any other electronic device described herein. The cover assembly 522 may define any suitable surface of the electronic device, such as a front surface or a rear surface.

The emitter module 582 and the receiver module 584 of the sensor 571 are positioned below the cover assembly 522 and are schematically illustrated with dashed lines in FIG. 5A. As shown in FIG. 5B, the emitter module 582 and the receiver module 584 may be spaced apart from the cover assembly 522 by a gap 561. In addition, the emitter module 582 and the receiver module 584 may be supported by a support 587.

As shown in FIG. 5A, the cover assembly 522 includes a cover member 532 and the cover member 532 includes a first region 542, a second region 544, and a third region 546. The first region 542 is positioned over the emitter module 582 and the second region 544 is positioned over the receiver module 584. A portion of the third region 546 is interposed between the first region 542 and the second region 544. As shown in the cross-section view of FIG. 5B, each of the first region 542, the second region 544, and the third region 546 may extend from an interior surface 551 to an exterior surface 553 of the cover member 632.

In the example of FIGS. 5A and 5B, the third region 546 surrounds the first region 542 and the second region 544. In some cases, a minimum lateral dimension of the portion of the third region interposed between the first region 542 and the second region 544 may be from 100 microns to 1 cm, from 250 microns to 5 mm, from 250 microns to 1 m, or from 500 microns to 5 mm. In some cases, a maximum lateral dimension of the third region may be up to 1 cm, up to 2 cm, up to 5 cm, or more.

The third region 546 comprises a glass ceramic material and typically comprises a different material than the first region 542 and the second region 544. The glass ceramic material of the third region 546 of the cover member may be configured to at least partially impede transmission of light over a specified wavelength range and reduce optical crosstalk as previously described with respect to FIGS. 3A-3C. The description of the first region 342, the second region 344, and the third region 346 provided with respect to FIGS. 3A-3C is applicable to first region 542, the second region 544, and the third region 546 and, for brevity, is not repeated here.

Figure 6A:
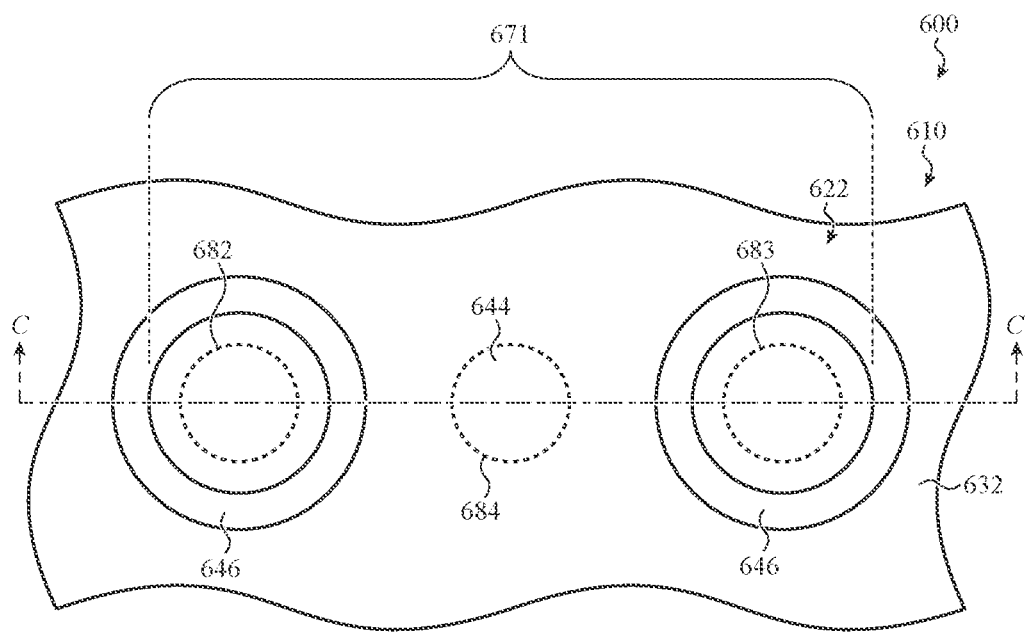
FIG. 6A shows a top view of an electronic device comprising an enclosure having multiple glass ceramic regions.

FIG. 6A shows a top view of an electronic device comprising an enclosure 610 having a multiple glass ceramic region regions. The electronic device 600 includes a cover member 632 including a first region 642, a second region 643, a third region 646, a fourth region 646, and a fifth region 647. The first region 642 is positioned over the emitter module 682, the second region 643 is positioned over the emitter module 683 and the third region 644 is positioned over the receiver module 684. The fourth region 646 and the fifth region 647 each include a glass ceramic material capable of at least partially optically isolating the receiver module 684 from the emitter modules 682 and 683 from as previously discussed with respect to FIG. 3C. In some cases, the cover member 632 may be a cover member of a wearable electronic device, such as the electronic device 1100.

As indicated in FIG. 6A, the two emitter modules 682 and 683 are part of the same sensor 671. In some cases the emitter module 682 is configured to emit a first optical signal and the emitter module 683 is configured to emit a second optical signal different than the first optical signal. The first optical signal may have a first sensor wavelength range and the second optical signal may have a second sensor wavelength range different than the first sensor wavelength range. For example, the first optical signal may be a first visible light signal and the second optical signal may be a second visible light signal different than the first visible light signal. In particular, the first optical signal may be a visible light signal and the second optical signal may be a near-IR signal. In some cases, the sensor 671 may be a health monitoring sensor (assembly), such as a photoplethysmogram (PPG) sensor. The PPG sensor may be adapted to operate as a heart rate sensor, a pulse oximeter, or other health sensor configured to measure a health characteristic or health metric of the user. Thus, the PPG sensor may detect a heart rate, an oxygen level, or both. However, this example is not limiting and in other examples the two emitter modules may be part of different sensors.

The emitter modules 682, 683 may share a receiver module 684 and/or the receiver module 684 may include multiple photosensitive elements that are responsive to different wavelengths of light. For example, the receiver module 684 may include multiple photodiodes that are each responsive to a different wavelength or band of wavelengths. In some cases, the receiver module 684 is responsive to a broad range of wavelengths, which may include light emitted from both emitter modules 682 and 683.

Figure 6B:
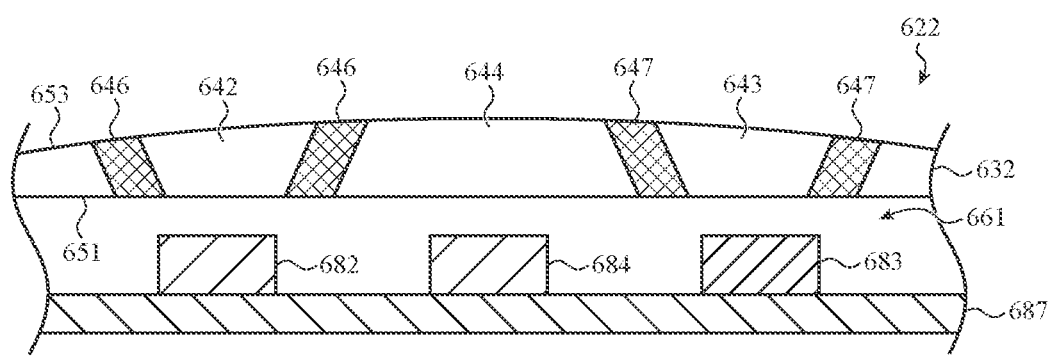
FIG. 6B shows a cross-section view of the electronic device of FIG. 6A.

FIG. 6B shows a cross section view of the electronic device 600 along C-C. The electronic device 600 may be an example of the electronic device 100 or of any other electronic device described herein. The cover assembly 622 may define any suitable surface of the electronic device, such as a front surface or a rear surface. The arrangement of the emitter modules 682 and 683 and the receiver module 684 is provided by way of illustrative example. However, the relative position of the modules may vary depending on the implementation. For example, in some implementations, the sensor 671 may use a single emitter and multiple receivers. The single emitter may include multiple light emitting elements that are configured to produce a same band of wavelengths or different bands of wavelengths or different discrete wavelengths, in accordance with the examples provided above.

The emitter modules 682 and 683 and the receiver module 684 are positioned below a cover assembly 622 and are schematically illustrated with dashed lines in FIG. 6A. As shown in FIG. 6B, the emitter module 682 and the receiver module 684 may be spaced apart from the cover assembly 622 by a gap 661. In addition, the emitter modules 682 and 683 and the receiver module 684 may be supported by a support 687. The description of the emitter module 382 is applicable to the emitter modules 682 and 683 and the description of the receiver module 384 is applicable to the receiver module 684. For brevity that description is not repeated here.

As shown in FIG. 6A, the cover assembly 622 includes a cover member 632 and the cover member 632 includes a first region 642, a second region 643, a third region 644, a fourth region 646, and a fifth region 647. In the example of FIG. 6B, the cover member 632 and the cover assembly 622 define a curve rather than a plane. In particular, the cover member 632 defines a convex outer surface 653. As shown in the cross-section view of FIG. 6B, each of the first region 642, the second region 643, the third region 644, the fourth region 646 and the fifth region 647 may extend from an interior surface 651 to an exterior surface 653 of the cover member 632. In the example of FIG. 6B the third region 644 is thicker than the first region 642 and the second region 643. However, this example is not limiting and in some examples the thickness may be uniform or a thickness of a central portion of the cover member may be greater than a thickness of a peripheral portion of the cover member (or vice versa).

As shown in FIG. 6B, the first region 642 is positioned so that a path of light emitted by the emitter 682 (also referred to herein as a light path) will pass through the first region 642. This light path may form a first oblique angle with respect to the thickness of the cover member 632. Similarly, the second region 643 is positioned so that the path of light emitted by the emitter 683 will pass through the second region 643. This light path may form a second oblique angle with respect to the thickness of the cover member 632. When the light paths are not parallel to the thickness of the cover member, the first region 642 may not be positioned directly over the emitter 682 and the second region 643 may not positioned directly over the emitter 683.

As shown in FIG. 6A, the fourth region 646 forms a ring surrounding the first region 642 and the fifth region 647 forms a ring surrounding the third region 643. It should be understood that this example is not limiting and that the fourth region 646 and the fifth region 647 may be configured in a variety of ways. As shown in FIG. 6B, the diameter of the rings formed by the fourth region 646 and the fifth region 647 decreases from the exterior surface 653 to the interior surface 651. As a result, a side of each of the first region 642 and the second region 643 may define a generally conical shape. The ring shape of the fourth region 646 and the fifth region 647 may be useful with a cover member 632 defining a curved exterior surface 653 as well as a cover member defining a planar exterior surface. In some cases, a lateral dimension of the fourth region 646 and the fifth region 647 may be from 100 microns to 1 cm, from 250 microns to 5 mm, from 250 microns to 1 m, or from 500 microns to 5 mm.

The fourth region 646 comprises a glass ceramic material and typically comprises a different material than the first region 642 and the third region 644. In addition, the fifth region 647 comprises a glass ceramic material and typically comprises a different material than the second region 643 and the third region 644. The glass ceramic material of the fourth region 646 and the fifth region 647 of the cover member may be configured to at least partially impede transmission of light over a specified wavelength range and reduce optical crosstalk as previously described with respect to FIGS. 3A-3C. The light transmission properties of the fourth region 646 and the fifth region 647 of the cover member can therefore allow closer spacing of the emitters and the receiver.

The description of the first region 342 provided with respect to FIGS. 3A-3C is applicable to the first region 642 and the second region 643. The description of the second region 344 provided with respect to FIGS. 3A-3C is applicable to the third region 644. The description of the third region 346 provided with respect to FIGS. 3A-3C is applicable to the fourth region 646 and the fifth region 647. For brevity that description is not repeated here.

Figure 7A:
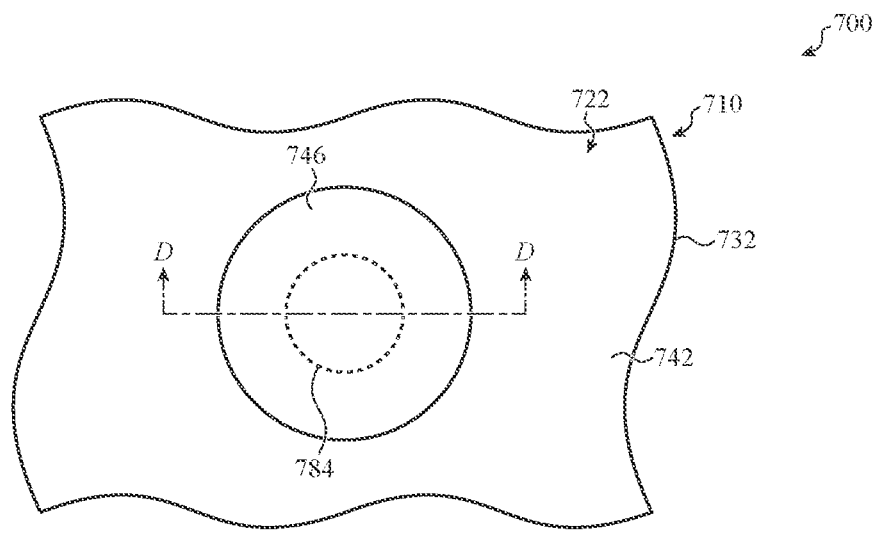
FIG. 7A shows a top view of another electronic device comprising an enclosure having a glass ceramic region.

FIG. 7A shows a top view of an electronic device comprising an enclosure 710 having a glass ceramic region. The electronic device includes a cover member 732 including a first region 742 and a second region 746 and an optical component 784 positioned under the second region 746. The second region 746 may comprise a glass ceramic material. The optical component 784 may be sensor assembly or a camera assembly or any optical component described herein. The electronic device 700 may be an example of the electronic device 100 or of any other electronic device described herein. The cover assembly 722 may define any suitable surface of the electronic device, such as a front surface or a rear surface.

Figure 7B:
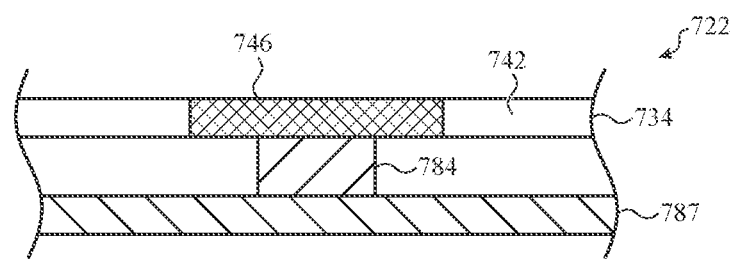
FIG. 7B shows a cross-section view of the electronic device of FIG. 7A.
Figure 7C:
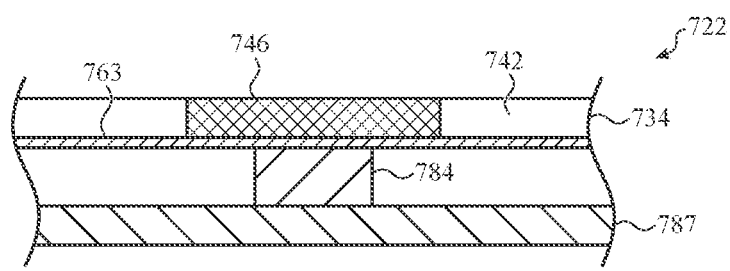
FIG. 7C shows an additional cross-section view of the portion of the electronic device of FIG. 7A.

In the example of FIGS. 7A-7C, the optical component 784 is configured to emit or detect light over a specified wavelength range which differs from the visible spectrum, such as an infrared (IR) light wavelength range, or an ultraviolet (UV) wavelength range. The glass ceramic material of the second region 746 is configured to transmit light in the specified wavelength range to a first extent and to transmit light in the visible spectrum to a second extent which is less than the first extent. As a result, the second region 746 at least partially obscures the optical component 784 from view by a user.

Figure 9A:
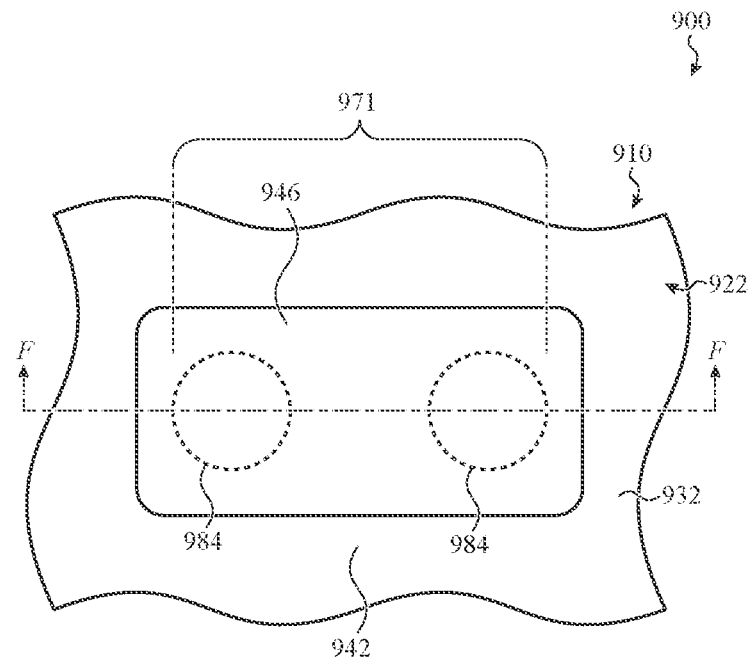
FIG. 9A shows a top view of a further electronic device comprising an enclosure having a glass ceramic region.

FIGS. 7B and 7C show example cross-section views of the portion of the electronic device of FIG. 7A along D-D. In the example of FIGS. 7A to 7C, the second region 746 forms a cylinder over the optical component 784 and the first region 742 surrounds the second region 746. It should be understood that this example is not limiting and that the second region 746 may have a cross-sectional shape which is circular, oval, rectangular, square, triangular, or the like. In addition, the second region 746 may form a generally conical shape similar to that previously shown in FIG. 6B. Further, the second region 746 may have a larger lateral dimension an example of which is shown in FIG. 9A. In addition, although the example of FIGS. 7A to 7C shows the second region 746 as extending through a thickness of the cover member 734, in other examples the second region 746 may extend through less than a thickness of the cover member. For example the second region may extend through one-half to three-quarters of the thickness or from one-quarter to one-half of the thickness.

The optical component 784 is positioned below the cover assembly 722 and is schematically illustrated with dashed lines in FIG. 7A. In the examples of FIGS. 7B and 7C, the optical component 784 may be supported by a support 787. In the example of FIG. 7B, the optical component 784 contacts the cover member 732 of the cover assembly 722. In the example of FIG. 7C, the optical component 784 may be spaced apart from the cover member by a coating 763 along an interior surface of the cover member 732. The coating 763 may be configured to further modify the appearance of the cover assembly 722 without substantially interfering with the optical component 784 as explained in more detail below. In other examples, the optical module may be spaced apart from the cover assembly 722 by a gap (as previously shown in FIG. 3B) or may extend into an opening in the cover assembly 722.

As previously mentioned, the optical component 784 may emit or detect light over a specified wavelength range and the second region 746 may be configured to transmit light in the specified wavelength range (which differs from the visible spectrum). In addition, the second region 746 may be configured to transmit light in the visible spectrum to a lesser extent than light in the specified wavelength range. Therefore, the second region 746 can at least partially obscure the optical component 784 from view while not significantly interfering with the operation of the optical component 784. In the example of FIG. 7C, the coating may also be configured to transmit light in the specified wavelength range while transmitting light in the visible spectrum to a lesser extent. Therefore, the coating may further obscure the optical component 784 from view. In some cases, the coating may be configured to absorb light in the visible spectrum without significantly absorbing light in the near infrared range. In some cases, the coating comprises a visibly absorbing infrared transparent pigment in a polymeric binder.

The extent to which a region of the cover member 732 transmits light can be measured by the transmittance of the region over a specified wavelength range. The transmittance can be measured as the total transmittance, the direct transmittance (also referred to as regular transmittance), the diffuse transmittance, or combinations thereof.

In some cases the second region 746 may have a transmittance of at least 60%, at least 70%, at least 80%, at least 85%, at least 90%, or at least 95% of the specified wavelength range, such as a near-IR range. The second region 746 may have a transmittance over the visible spectrum that is less than or equal to 50%, less than or equal to 40%, less than or equal to 30%, or less than or equal to 20%.

The first region 742 may have a transmittance different from the second region 746. In some cases, the transmittance of the first region 742 is greater than the transmittance of the second region 746 over the visible spectrum. For example, the first region 742 may appear transparent or less translucent than the second region 746. The transmittance of the first region 742 over the visible spectrum may be at least 60%, at least 70%, at least 80%, at least 85%, at least 90%, or at least 95%.

In additional cases, the transmittance of the first region 742 may be less than the transmittance of the second region 746 over the specified wavelength range and over the visible range. For example, the first region 742 may be used to optically isolate the second region 746 of the cover member 732 by at least partially impeding transmission of light through the first region 742 in a similar fashion as previously described with respect to FIG. 3C. The first region 742 may have a transmittance over the specified wavelength range or the visible spectrum that is less than or equal to 50%, less than or equal to 40%, less than or equal to 30%, or less than or equal to 20%.

The internal structure of the glass ceramic material of the second region 746 may be configured to transmit light in the specified wavelength range and to transmit light in the visible spectrum to a lesser extent. The internal structure of a region of the cover member may be characterized at least in part by one or more phase(s) present in the region, a characteristic length scale of the phase(s) (e.g., a size of a crystalline phase present in the region), and a characteristic amount of the one or more phase(s). The internal structure may also be referred to as a microstructure or a nanostructure (when the characteristic length scale is from about 1 nm to about 100 nm). In some examples, the first region 742 may have an internal structure configured to transmit the light in the visible spectrum to a greater extent than the second region 746, so that the region 742 is transparent.

In the example of FIGS. 7A-7C, the second region 746 comprises a glass ceramic material which includes a crystalline phase. In some cases, at least some of the crystals in the second region 746 may have a size which scatters light over all or part of the visible spectrum, but scatters light of longer wavelengths to a lesser extent. For example, near-IR wavelengths of light, such from about 800 nm to about 2.5 microns, from 900 nm to about 1.6 microns, or from about 800 nm to about 1000 nm, may be scattered to a lesser extent than visible light wavelengths (in a visible spectrum from about 380 nm to about 740 nm).

As a particular example, the crystals in the second region 746 may be sized to scatter light in the visible spectrum though Mie scattering, but may be sized to scatter light in a near-IR wavelength range to a lesser extent through Mie scattering. In some cases, the second region 746 may predominantly include crystals having a size (e.g., a diameter) which is less than or equal to a multiplier of a near-IR wavelength of light, such a multiplier of about 0.06 or 0.1. In addition, at least some of the crystals in in the second region 746 may have a size (e.g., a diameter) which is greater than or equal to a multiplier of a visible light wavelength, such a multiplier of about 0.1 or 0.3. For example, a median crystal size of the second region 746 may be from about 30 nm to about 80 nm, from about 50 nm to about 100 nm, or from about 90 nm to about 150 nm.

The second region 746 comprises a glass ceramic material which is different from the material of the first region 742. In some cases, the first region is a glass region. In additional cases, the first region 742 comprises nuclei for crystallization dispersed in a crystallizable glass. The nuclei may be as previously described with respect to FIGS. 3A to 3C and, for brevity, that description is not repeated here. In further cases, the glass ceramic material of the first region 742 different from the glass ceramic material of the second region 746. For example, the first region 742 may have a different median crystal size than the second region 746. When the median crystal size of the first region 742 is smaller than that of the second region the first region 742 may have a higher transmittance for visible light than the second region. In addition, when the median crystal size of the first region 742 is larger than that of the second region the first region may have a lower transmittance for IR light than the second region. Alternately or additionally, the glass first region 742 has at least one crystalline phase that differs from the crystalline phase(s) in the second region 742. The description of glasses and glass ceramics provided with respect to FIGS. 3A to 3C is generally applicable herein and, for brevity, are not repeated here.

A cover member comprising a glass ceramic second region 746 different from the first region 742 can be formed by locally modifying a precursor of the cover member to form the second region. When the precursor member is formed of a single piece of material the cover member is also integrally formed. The precursor member may be locally modified by locally applying energy to at least one region of the precursor member. For example, the at least one region of the precursor member may be locally heated with a laser or other localized source of heat. The methods for locally applying energy described with respect to FIGS. 3A to 3C are generally applicable herein and, for brevity, are not repeated here.

In some cases, the precursor member comprises a crystallizable glass and the local modification of the precursor member comprises locally forming crystals in a crystallizable glass member. In additional cases, the precursor member comprises nuclei for crystallization (e.g., nuclei formed from one or more nucleating agents) dispersed in a crystallizable glass. The precursor member may be substantially free of a crystalline phase formed from the principal elements of the glass ceramic (also referred to as a principal crystalline phase) or only a small amount of the principal crystalline phase may be present in the precursor. In additional cases, the precursor member comprises a glass ceramic comprising a crystalline phase and local modification of the precursor member comprises locally growing crystals of the same crystalline phase, locally forming crystals of a different crystalline phase, or combinations thereof. The description of precursor members, local modification of precursor members, and glass ceramic materials with respect to FIGS. 3A to 3C is generally applicable herein and, for brevity, is not repeated here.

Figure 8A:
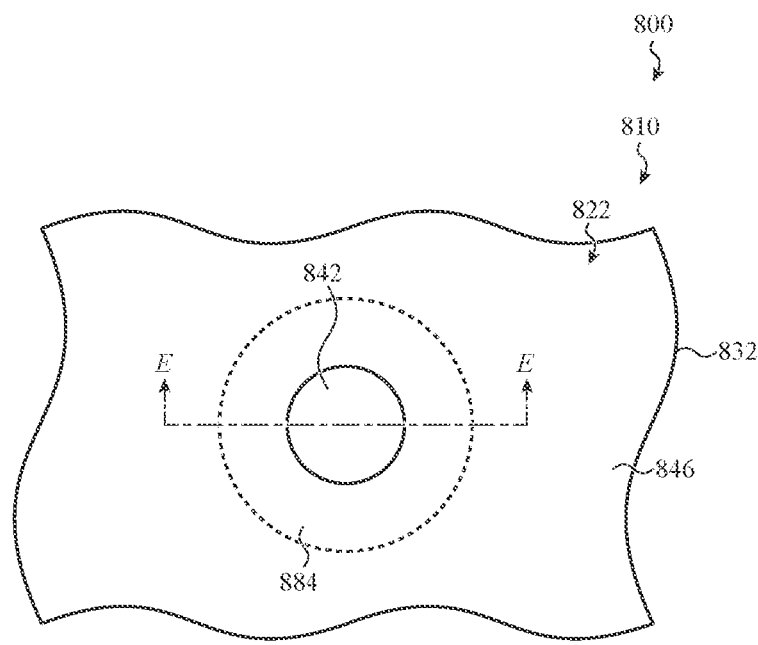
FIG. 8A shows a top view of an additional electronic device comprising an enclosure having a glass ceramic region.

FIG. 8A shows a top view of an electronic device comprising an enclosure 810 having a glass ceramic region. The electronic device includes a cover member 822 including a first region 842 and a second region 846 and an optical component 884 positioned under the first region 842 and a portion of the second region 846. The second region 846 may comprise a glass ceramic material. The optical component 884 may be a sensor assembly, a camera assembly, or any other optical component described herein. The electronic device 800 may be an example of the electronic device 100 or of any other electronic device described herein. The cover assembly 822 may define any suitable surface of the electronic device, such as a front surface or a rear surface.

Figure 8B:
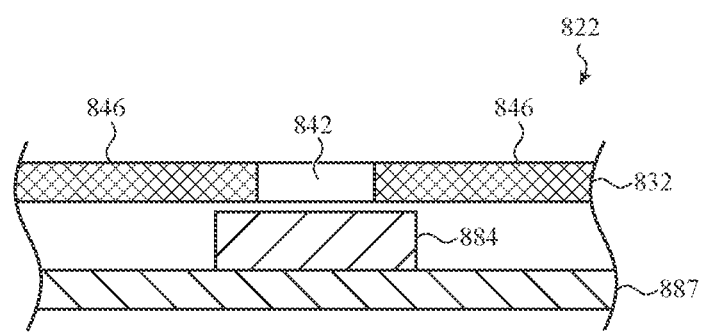
FIG. 8B shows a cross-section view of the electronic device of FIG. 8A.

FIG. 8B shows an example cross-section view of the portion of the electronic device of FIG. 8A along E-E. As shown in FIGS. 8A to 8B, the first region 842 and a portion of the second region 842 are positioned over the optical component 884. The portion of the second region 846 may be positioned over a peripheral region of the optical component 884 and the first region 842 may be positioned over a central region of the optical module. The central region of the optical component 884 may correspond to an aperture of the optical module. In the examples of FIGS. 8A and 8B, the optical component 884 may be supported by a support 887

In some cases, the optical component 884 may be configured to emit or detect light over a specified wavelength range. When the specified wavelength range differs from the visible spectrum, the second region 846 may include a glass ceramic material configured to transmit light in the specified wavelength range to a first extent and to transmit light in the visible spectrum to a lesser extent. Because the second region 846 transmits light over the specified wavelength range, the field of view of the emitter and/or receiver module need not be substantially limited by the presence of the second region. The first region 842 may be configured to transmit light in both the specified wavelength range and in the visible spectrum. When optical component 884 is configured to emit or detect light over the visual spectrum, the second region 846 may simply be configured to provide transmit light over the visual spectrum to a lesser extent than the first region 842.

In the example of FIGS. 8A to 8B, the first region 842 forms a cylinder over the optical component 884 and the second region 846 surrounds the first region 842. It should be understood that this example is not limiting and that the first region 842 may have a cross-sectional shape which is circular, oval, rectangular, square, triangular, or the like. Further, the first region 842 may be generally conical in shape. In addition, although the example of FIGS. 8A to 8B shows the second region 846 as extending through a thickness of the cover member 832, in other examples the second region 846 may extend through less than a thickness of the cover member. For example the second region may extend through one-half to three-quarters of the thickness or from one-quarter to one-half of the thickness.

The optical component 884 may be an example of the optical module 746, the first region 842 may have similar properties and may be formed in a similar fashion as previously described for the first region 742 and the second region 846 may have similar properties and may be formed in a similar fashion as previously described for the first region 746. For brevity, the description provided with respect to the optical module 746, the first region 742, and the second region 746 is not repeated here.

FIG. 9A shows a top view of an electronic device 900 comprising an enclosure 910 having a glass ceramic region. The electronic device 900 includes a cover member 932 including a first region 942 and a second region 946. The second region 846 may comprise a glass ceramic material. A sensor assembly 971 includes an emitter module 982 and a receiver module 984 positioned below the second region 946. The electronic device 900 may be an example of the electronic device 100 or of any other electronic device described herein. The cover assembly 922 may define any suitable surface of the electronic device, such as a front surface or a rear surface.

Figure 9B:
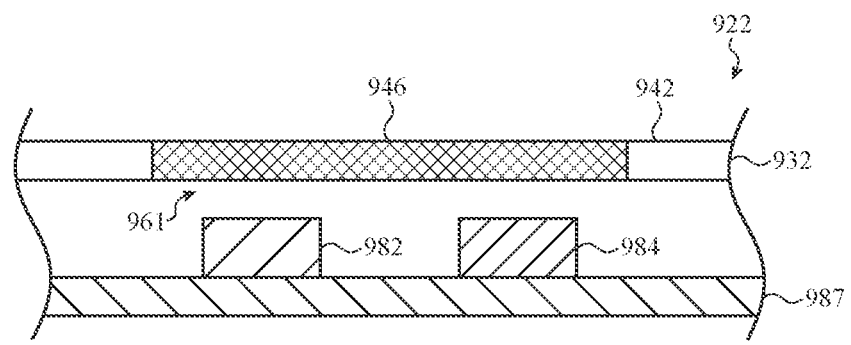
FIG. 9B shows a cross-section view of the electronic device of FIG. 9A

In the example of FIGS. 9A and 9B, the emitter module 982 is configured to emit light over a specified wavelength range which differs from the visible spectrum, such as an infrared (IR) light wavelength range or an ultraviolet (UV) wavelength range. The receiver module 984 is configured to detect light from the emitter module. The second region 946 includes a glass ceramic material configured to transmit light in the specified wavelength range to a first extent and to transmit light in the visible spectrum to a lesser extent, thereby at least partially obscuring the emitter module 982 and the receiver module 984 from view by a user.

The emitter module 982 and the receiver module 984 of the sensor 971 are positioned below a cover assembly 922 and are schematically illustrated with dashed lines in FIG. 9A. FIG. 9B shows a cross section view of the electronic device 900 along F-F. The shape of the emitter module 982 and of the receiver module 984 are not limited to the shapes shown in the example of FIGS. 9A and 9B, but can be any suitable shape, including a rectangular prism, a cube, or a cylinder. The sensor 971 may be configured to operate in a reflective sensing mode as was previously described with respect to FIG. 3C.

As shown in FIG. 9B, the emitter module 982 and the receiver module 984 may be spaced apart from the cover assembly 922 by a gap 961. In addition, the emitter module 982 and the receiver module 984 may be supported by a support 987. It should be understood that the form of the support 987 is not limiting and that the sensor 971 may include additional elements not shown in FIG. 9B, such as circuitry and additional packaging for the emitter and receiver modules.

The first region 942 may have similar properties and may be formed in a similar fashion as previously described for the first region 742. The second region 946 may have similar properties and may be formed in a similar fashion as previously described for the first region 746. For brevity, the description provided with respect the first region 742 and the second region 746 is not repeated here.

FIG. 10 shows another example of an electronic device 1000 comprising an enclosure 1010 having a glass ceramic region. The electronic device 1000 includes a first portion 1002 and a second portion 1004. The first portion 1002 may comprise display 1011 positioned within a housing 1012. A cover assembly 1022 is provided over the display 1011. The second portion 1004 may comprise a housing 1014, a keyboard 1016, and a trackpad 1017. The electronic device 1000 may be a laptop or notebook computing device in which the first portion 1002 is coupled to the second portion 1004 by a hinge 1003. Alternately, the first portion 1002 of the electronic device 1000 may be a tablet computing device and the second portion 1004 may be removably coupled to the first portion 1002. In some cases, the second portion 1004 is configurable to form a case for the tablet computing device.

In the example of FIG. 10, the first portion 1002 includes a cover assembly 1022 which comprises a sensor area 1018. The electronic device 1000 may include one or more optical components located in the vicinity of the sensor area 1018. In some cases, an optical module of a sensor or camera assembly may be positioned below the cover assembly 1022. In additional cases, an optical module of a sensor or camera assembly (e.g., a camera module) may be positioned at least partially within an opening in the cover assembly 1022. Alternately or additionally, the second portion 1004 of the electronic device may include a sensor area. For example, a sensor area may be included as part of the keyboard 1016 or the trackpad 1017. The description of optical components, sensor assemblies and camera assemblies provided with respect to FIGS. 1A to 3C is generally applicable herein and, for brevity, is not repeated here.

In some cases, the cover assembly 1022 includes a cover member including a glass ceramic region. In some examples, the glass ceramic region of the cover member is configured to at least partially optically isolate an emitter module from a receiver module, as previously described with respect to FIGS. 3A to 3C. In additional examples, the glass ceramic region of the cover is configured to obscure visual observation of an emitter module and/or a receiver module configured to operate over a different wavelength range (e.g., a near-IR wavelength range), as previously described with respect to FIGS. 7A to 9B. The description provided with respect to FIGS. 3A to 3C and 7A to 9B is generally applicable herein and, for brevity, is not repeated here.

FIG. 11 shows an additional example of an electronic device 1100 comprising an enclosure 1110 having a glass ceramic region. The electronic device 1100 includes a housing 1112, a cover assembly 1122 and a cover member 1132. The electronic device 1100 may be a wearable electronic device such as watch. The housing 1012 and the cover assembly 1122 may define a rear surface of the wearable electronic device. For example, the rear surface of the wearable electronic device may contact the skin of a user when the device is worn. The electronic device further includes input devices 1105 and 1107.

As shown in FIG. 11, the cover assembly 1122 comprises a sensor area 1118. The electronic device 1100 may include one or more sensor assemblies located in the vicinity of the sensor area 1118. For example, the one or more sensor assemblies may be one or more health monitoring sensor assemblies or biosensor assemblies, such an electrocardiogram (ECG) sensor, a photoplethysmogram (PPG) sensor, heart rate sensor, a pulse oximeter or other bio-sensor. In the example of FIG. 11, the electronic device 1100 includes two emitter modules 1182 and 1183 and two receiver modules 1184 and 1185. However, this example is not limiting and the electronic device may include a greater or a lesser number of emitter modules and/or receiver modules. Further, the arrangement of emitter modules and receiver modules is not limited to that shown in FIG. 11. In additional examples the receiver modules may be positioned closer to a periphery of the cover assembly 1122 than the emitter modules and may positioned so as to surround the emitter modules (e.g., may be positioned along a ring surrounding the emitter modules). For example, the sensor may define a central emitter region located near or at the center of the cover assembly 1122. The sensor may also define an array of receiver regions that surround the central emitter region, each receiver region having one or more receiver modules positioned below the cover assembly 1122. Other emitter/receiver module arrangements may also be used.

In some cases the emitter module 1182 is configured to emit a first optical signal and the emitter module 1183 is configured to emit a second optical signal different than the first optical signal. The second optical signal may have a second sensor wavelength range which is different from a first sensor wavelength range of the first optical signal.

The electronic device may include one or more emitter modules which emit light over at least a portion of the visible spectrum (e.g., green light and/or red light), in which case the optical signal may be a visible (light) signal. The electronic device may further include one or more emitter modules which emit light over a near-IR wavelength range, in which case the optical signal may be a near-IR (light) signal. For example, a heart rate biosensor may include an emitter module which produces a visible light signal (e.g., green light) and an emitter module which produces an infrared light signal. As another example, a pulse oximetry biosensor (e.g., an SpO$_2$ sensor) may include one or more emitter modules which produce an optical signal over a wavelength range at which the absorption of oxygenated hemoglobin and deoxygenated hemoglobin is different (e.g., red light) and one or more emitter modules which produce an optical signal over a wavelength range at which the absorption of oxygenated hemoglobin and deoxygenated hemoglobin is similar (e.g., green light or infrared light).

As previously mentioned, the electronic device may further include a processing unit, also referred to herein as a processor. When sensor assembly is a biosensor assembly, the processing unit may be configured to compute a health metric or health characteristic associated with the user based on a signal from the sensor. For example, the health metric computed based on an optical biosensor (e.g., a PPG sensor) assembly may be a heart rate and/or a peripheral oxygen saturation (SpO$_2$) value. The device may also include a display disposed within the housing and configured to display the health metric.

In some cases, the cover assembly 1122 includes a cover member 1132 including a glass ceramic region. In some examples, the glass ceramic region of the cover member 1132 is configured to at least partially optically isolate an emitter module from a receiver module. In some examples a single glass ceramic region may be used to isolate the emitter modules (e.g. 1182, 1183) from the receiver modules (e.g., 1185, 1185). In additional examples, the cover member 1132 may include multiple glass ceramic regions. Each of the emitter regions may be surrounded by a glass ceramic region, as illustrated in FIGS. 6A and 6B or each of the receiver regions may surrounded by a glass ceramic region. In additional examples, the glass ceramic region of the cover member 1132 is configured to obscure visual observation of an emitter module and/or a receiver module configured to operate over a different wavelength range (e.g., a near-IR wavelength range), as previously described with respect to FIGS. 7A to 9B. The description provided with respect to FIGS. 3A to 3C and 7A to 9B is generally applicable herein and, for brevity is not repeated here.

As shown in FIG. 11, the enclosure 1110 that includes a housing 1112 that defines a rear surface 1104 of the electronic device 1100 and a curved side surface 1106 that extends from the bottom surface to a top surface. The cover member 1132 may be provided along the rear surface of the electronic device. The rear surface of the electronic device 1100 may be substantially flat. A band 1170 may be attached to the housing and configured to secure the wearable electronic device to a user (in FIG. 11, the band 1170 is curved to show the rear surface 1104). The enclosure 1110 may define a cavity and the housing 1112 may define an opening to the cavity. A display, such as a touch-sensitive display, may be at least partially disposed within the cavity and may have a viewable area. The device may also include a front cover member disposed above the display and including a flat middle portion larger than the viewable area of the display, a curved edge portion surrounding the flat middle portion and coinciding with the curved side portion along a perimeter of the cavity to form a continuous contoured surface.

The electronic device 1100 may further include a crown module that is positioned at least partially within an aperture formed within the curved side portion of the housing. The crown module may include an input member 1105 (e.g., a dial) having an outer surface configured to receive a rotary user input. The crown module may be offset with respect to a centerline of the housing between the top portion and the flat bottom portion. The offset may be toward the top portion of the housing. The crown module may include a dial having a portion that is higher than an interface between the cover and the housing.

In some example embodiments, the device includes a biosensor assembly that is disposed in an opening formed in the rear surface of the housing. The biosensor assembly may include a chassis positioned in the opening of the housing. The emitter module(s) and receiver module(s) may be attached to the chassis. The cover member 1132 is disposed over the chassis and over the emitter module(s) and receiver module(s). In some embodiments, the cover member 1132 has a convex outer contour. For example, the cover member 1132 may have a shape similar to that shown in FIG. 6B.

FIG. 12 shows a top view of an electronic device 1200 comprising an enclosure 1210 having a glass ceramic region. The electronic device 1200 includes a housing 1212 and a cover member 1222. The electronic device 1200 may be a portable media player such as a smart speaker. The housing 1212 and the cover member 1222 may define a top of electronic device.

The electronic device 1200 may include one or more sensor assemblies located in the vicinity of the sensor area 1218. In the example of FIG. 12, the electronic device 1200 includes four sensor assemblies 1271, 1272, 1273, and 1274. One or more of the sensor assemblies 1271, 1272, 1273, and 1274 may include one or more emitter modules which emit light over a near-IR wavelength range. In some cases, at least one of the sensor assemblies 1271, 1272, 1273, and 1274 is a proximity sensor, a time of flight sensor, a biometric identification sensor, or the like. The description of emitter modules and receiver modules provided with respect to FIGS. 1A to 3C is generally applicable herein and, for brevity, is not repeated here. The electronic device 1200 may further include an emitter module 1275.

In some cases, the cover assembly 1222 includes a cover member 1232 including a glass ceramic region. In some examples, the glass ceramic region of the cover member is configured to at least partially optically isolate an emitter module from a receiver module, as previously described with respect to FIGS. 3A to 3C. In additional examples, the glass ceramic region of the cover is configured to obscure visual observation of an emitter module and/or a receiver module configured to operate over a different wavelength range (e.g., a near-IR wavelength range), as previously described with respect to FIGS. 7A to 9B. The description provided with respect to FIGS. 3A to 3C and 7A to 9B is generally applicable herein and, for brevity, is not repeated FIG. 13 shows a block diagram of components of an electronic device. The schematic representation depicted in FIG. 13 may correspond to components of the devices depicted in FIGS. 1A to 12 as described above. However, FIG. 13 may also more generally represent other types of electronic devices with cover assemblies as described herein.

In embodiments, an electronic device 1300 may include sensors 1320 to provide information regarding configuration and/or orientation of the electronic device in order to control the output of the display. For example, a portion of the display 1308 may be turned off, disabled, or put in a low energy state when all or part of the viewable area of the display 1308 is blocked or substantially obscured. As another example, the display 1308 may be adapted to rotate the display of graphical output based on changes in orientation of the device 1300 (e.g., 90 degrees or 180 degrees) in response to the device 1300 being rotated.

The electronic device 1300 also includes a processor 1306 operably connected with a computer-readable memory 1302. The processor 1306 may be operatively connected to the memory 1302 component via an electronic bus or bridge. The processor 1306 may be implemented as one or more computer processors or microcontrollers configured to perform operations in response to computer-readable instructions. The processor 1306 may include a central processing unit (CPU) of the device 1300. Additionally, and/or alternatively, the processor 1306 may include other electronic circuitry within the device 1300 including application specific integrated chips (ASIC) and other microcontroller devices. The processor 1306 may be configured to perform functionality described in the examples above.

The memory 1302 may include a variety of types of non-transitory computer-readable storage media, including, for example, read access memory (RAM), read-only memory (ROM), erasable programmable memory (e.g., EPROM and EEPROM), or flash memory. The memory 1302 is configured to store computer-readable instructions, sensor values, and other persistent software elements.

The electronic device 1300 may include control circuitry 1310. The control circuitry 1310 may be implemented in a single control unit and not necessarily as distinct electrical circuit elements. As used herein, "control unit" will be used synonymously with "control circuitry." The control circuitry 1310 may receive signals from the processor 1306 or from other elements of the electronic device 1300.

As shown in FIG. 13, the electronic device 1300 includes a battery 1314 that is configured to provide electrical power to the components of the electronic device 1300. The battery 1314 may include one or more power storage cells that are linked together to provide an internal supply of electrical power. The battery 1314 may be operatively coupled to power management circuitry that is configured to provide appropriate voltage and power levels for individual components or groups of components within the electronic device 1300. The battery 1314, via power management circuitry, may be configured to receive power from an external source, such as an alternating current power outlet. The battery 1314 may store received power so that the electronic device 1300 may operate without connection to an external power source for an extended period of time, which may range from several hours to several days.

In some embodiments, the electronic device 1300 includes one or more input devices 1318. The input device 1318 is a device that is configured to receive input from a user or the environment. The input device 1318 may include, for example, a push button, a touch-activated button, capacitive touch sensor, a touch screen (e.g., a touch sensitive display or a force sensitive display), capacitive touch button, dial, crown, or the like. In some embodiments, the input device 1318 may provide a dedicated or primary function, including, for example, a power button, volume buttons, home buttons, scroll wheels, and camera buttons.

The device 1300 may also include one or more sensors 1320, such as a force sensor, a capacitive sensor, an accelerometer, a barometer, a gyroscope, a proximity sensor, a light sensor, or the like. The sensors 1320 may be operably coupled to processing circuitry. In some embodiments, the sensors 1320 may detect deformation and/or changes in configuration of the electronic device and be operably coupled to processing circuitry that controls the display based on the sensor signals. In some implementations, output from the sensors 1320 is used to reconfigure the display output to correspond to an orientation or folded/unfolded configuration or state of the device. Example sensors 1320 for this purpose include accelerometers, gyroscopes, magnetometers, and other similar types of position/orientation sensing devices. In addition, the sensors 1320 may include a microphone, acoustic sensor, light sensor (including ambient light, infrared (IR) light, ultraviolet (UV) light, optical facial recognition sensor, a depth measuring sensor (e.g., a time of flight sensor), a health monitoring sensor (e.g., an electrocardiogram (ECG) sensor, a heart rate sensor, a photoplethysmogram (PPG) sensor, a pulse oximeter, a biometric sensor (e.g., a fingerprint sensor), or other types of sensing device.

In some embodiments, the electronic device 1300 includes one or more output devices 1304 configured to provide output to a user. The output device 1304 may include display 1308 that renders visual information generated by the processor 1306. The output device 1304 may also include one or more speakers to provide audio output. The output device 1304 may also include one or more haptic devices that are configured to produce a haptic or tactile output along an exterior surface of the device 1300.

The display 1308 may provide graphical output. The display 1308 may include a liquid-crystal display (LCD), a light-emitting diode (LED) display, an LED-backlit LCD display, an organic light-emitting diode (OLED) display, an active layer organic light-emitting diode (AMOLED) display, an organic electroluminescent (EL) display, an electrophoretic ink display, or the like. If the display 1308 is a liquid-crystal display or an electrophoretic ink display, the display 1308 may also include a backlight component that can be controlled to provide variable levels of display brightness. If the display 1308 is an organic light-emitting diode or an organic electroluminescent-type display, the brightness of the display 1308 may be controlled by modifying the electrical signals that are provided to display elements. In addition, information regarding configuration and/or orientation of the electronic device may be used to control the output of the display as described with respect to input devices 1318. In some cases, the display is integrated with a touch and/or force sensor in order to detect touches and/or forces applied along an exterior surface of the device 1300 and may be referred to as a touch sensitive display.

The electronic device 1300 may also include a communication port 1312 that is configured to transmit and/or receive signals or electrical communication from an external or separate device. The communication port 1312 may be configured to couple to an external device via a cable, adaptor, or other type of electrical connector. In some embodiments, the communication port 1312 may be used to couple the electronic device 1300 to a host computer.

The electronic device 1300 may also include at least one accessory 1316, such as a camera, a flash for the camera, or other such device. The camera may be part of a camera assembly that may be connected to other parts of the electronic device 1300 such as the control circuitry 1310.

As used herein, the terms "about," "approximately," "substantially," "similar," and the like are used to account for relatively small variations, such as a variation of +/−10%, +/−5%, +/−2%, or +/−1%. In addition, use of the term "about" in reference to the endpoint of a range may signify a variation of +/−10%, +/−5%, +/−2%, or +/−1% of the endpoint value. In addition, disclosure of a range in which at least one endpoint is described as being "about" a specified value includes disclosure of the range in which the endpoint is equal to the specified value.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

The following discussion applies to the electronic devices described herein to the extent that these devices may be used to obtain personally identifiable information data. It is well understood that the use of personally identifiable information should follow privacy policies and practices that are generally recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not intended to be exhaustive or to limit the embodiments to the precise forms disclosed. It will be apparent to one of ordinary skill in the art that many modifications and variations are possible in view of the above teachings.

What is claimed is:

1. An electronic device comprising:
   a display;
   a reflectance sensor assembly comprising:
      an emitter module configured to emit an optical signal; and
      a receiver module configured to detect a reflection of the optical signal; and
   an enclosure enclosing the display and including a cover member positioned over the reflectance sensor assembly, the cover member comprising:
      an emitter region configured to transmit the optical signal emitted from the emitter module and comprising a first glass ceramic material having a first median crystal size;
      a receiver region configured to transmit the reflection of the optical signal to the receiver module and comprising a second glass ceramic material having a second median crystal size; and
      a glass ceramic region positioned between the emitter region and the receiver region, configured to impede transmission of the optical signal, and having an internal structure configured to scatter the optical signal and a third median crystal size greater than each of the first median crystal size and the second median crystal size.

2. The electronic device of claim 1, wherein each of the first glass ceramic material and the second glass ceramic material comprises a glass phase.

3. The electronic device of claim 1, wherein:
   the optical signal is a visible light signal; and
   each of the emitter region and the receiver region is transparent to visible light.

4. The electronic device of claim 1, wherein the optical signal is an infrared light signal having a wavelength from 800 nm to 1.6 microns.

5. The electronic device of claim 1, wherein the glass ceramic region surrounds the emitter region.

6. The electronic device of claim 1, wherein the glass ceramic region surrounds the receiver region.

7. The electronic device of claim 1, wherein crystals of the third glass ceramic material define a size gradient including smaller crystals at a periphery of the glass ceramic region.

8. The electronic device of claim 1, wherein the first, the second, and the third glass ceramic material each includes a same principal crystalline phase.

9. An electronic device comprising:
   a display;
   a sensor assembly including:
      an optical emitter module configured to emit an optical signal comprising light within a sensor wavelength range; and
      an optical receiver module configured to detect light within the sensor wavelength range; and
   an enclosure enclosing the display and the sensor assembly, the enclosure including a cover member formed of a glass ceramic material comprising a plurality of crystals and including:
      a first region positioned over the optical emitter module, having a first transmittance for light within the sensor wavelength range, and having a first median crystal size;
      a second region positioned over the optical receiver module, having a second transmittance for light within the sensor wavelength range, and having a second median crystal size; and
      a third region positioned between the optical emitter module and the optical receiver module, having a third transmittance for light within the sensor wavelength range, the third transmittance less than the first transmittance and the second transmittance, and having a third median crystal size greater than each of the first and the second median crystal size.

10. The electronic device of claim 9, wherein the glass ceramic region impedes optical crosstalk between the optical emitter module and the optical receiver module.

11. The electronic device of claim 9, wherein:
each of the first transmittance and the second transmittance is greater than 70%; and
the third transmittance is less than 50%.

12. The electronic device of claim 9 wherein:
at least some of the crystals in the third region scatter light in the sensor wavelength range.

13. The electronic device of claim 9 wherein:
the sensor wavelength range is an infrared range;
the first region has a transmittance for visible light less than the first transmittance; and
the second region has a transmittance for visible light less than the second transmittance.

14. An electronic device comprising:
a touch sensitive display;
a sensor assembly comprising;
    an optical emitter module configured to emit an optical signal comprising light in a wavelength range; and
    an optical receiver module configured to detect a reflection of the optical signal; and
an enclosure enclosing the touch sensitive display and the optical receiver module, the enclosure including a cover member comprising:
    an emitter region configured to transmit the optical signal and comprising a first glass ceramic material including a first set of crystals;
    a receiver region configured to transmit the reflection of the optical signal and comprising a second glass ceramic material including a second set of crystals; and
    a glass ceramic region configured to impede transmission of the optical signal within the cover member from the emitter region to the receiver region and comprising a third glass ceramic material including a third set of crystals, at least some of the crystals of the third set sized to scatter light in the wavelength range, and the crystals of the third set having a median size that is greater than a median size of the crystals of the first and the second sets.

15. The electronic device of claim 14, wherein:
the optical emitter module is a first optical emitter module, the optical signal is a first optical signal, and the emitter region is a first emitter region;
the sensor assembly further comprises a second optical emitter module configured to produce a second optical signal, different than the first optical signal;
the optical receiver module is further configured to detect the second optical signal; and
the cover member further comprises a second emitter region configured to transmit the second optical signal and comprising a fourth glass ceramic material including a fourth set of crystals.

16. The electronic device of claim 15, wherein:
the glass ceramic region is further configured to impede transmission of the second optical signal within the cover member from the second emitter region to the receiver region; and
the median size of the crystals of the third set is greater than a median size of the crystals of the fourth set.

17. The electronic device of claim 15, wherein:
the glass ceramic region is a first glass ceramic region;
a second glass ceramic region is configured to impede transmission of the second optical signal within the cover member from the second emitter region to the receiver region and includes a fifth set of crystals; and
a median size of the crystals of the fifth set is greater than a median size of the crystals of the fourth set.

18. The electronic device of claim 15, wherein:
the first optical signal is a first visible optical signal; and
the second optical signal is a second visible optical signal different from the first visible optical signal.

19. The electronic device of claim 15, wherein:
the first optical signal is a visible optical signal; and
the second optical signal is an infrared optical signal.

20. The electronic device of claim 15, wherein:
the electronic device is a wearable electronic device;
the cover member is positioned along a rear surface of the electronic device; and
the sensor assembly is a health monitoring sensor assembly.

* * * * *